US009993491B2

(12) United States Patent
Mulhbacher et al.

(10) Patent No.: US 9,993,491 B2
(45) Date of Patent: Jun. 12, 2018

(54) GUANINE RIBOSWITCH BINDING COMPOUNDS AND THEIR USE AS ANTIBIOTICS

(71) Applicant: SOCPRA—SCIENCES ET GENIE S.E.C., Sherbrooke (CA)

(72) Inventors: Jerome Mulhbacher, Sherbrooke (CA); Daniel Lafontaine, Sherbrooke (CA); Francois Malouin, Eastman (CA); Marianne Allard, Sherbrooke (CA); Eric Marsault, Sherbrooke (CA)

(73) Assignee: SOCPRA—SCIENCES ET GÉNIE S.E.C., Sherbrooke (CA)

( * ) Notice: Subject to any disclaimer, the term of this patent is extended or adjusted under 35 U.S.C. 154(b) by 0 days. days.

(21) Appl. No.: 14/616,164

(22) Filed: Feb. 6, 2015

(65) Prior Publication Data
US 2015/0150890 A1    Jun. 4, 2015

Related U.S. Application Data

(63) Continuation of application No. 13/377,052, filed as application No. PCT/CA2010/000868 on Jun. 14, 2010, now abandoned.

(60) Provisional application No. 61/186,669, filed on Jun. 12, 2009, provisional application No. 61/307,088, filed on Feb. 23, 2010.

(51) Int. Cl.
| *A61K 31/505*  | (2006.01) |
| *A61K 31/513*  | (2006.01) |
| *A61K 31/675*  | (2006.01) |
| *A61K 31/54*   | (2006.01) |
| *A61K 31/535*  | (2006.01) |
| *A61K 31/542*  | (2006.01) |
| *A61K 31/519*  | (2006.01) |
| *A61K 31/5383* | (2006.01) |
| *A61K 31/4412* | (2006.01) |
| *C07D 239/46*  | (2006.01) |
| *C07D 239/48*  | (2006.01) |
| *C07D 239/50*  | (2006.01) |
| *C07D 498/04*  | (2006.01) |
| *C07D 513/04*  | (2006.01) |

(52) U.S. Cl.
CPC ........ *A61K 31/675* (2013.01); *A61K 31/4412* (2013.01); *A61K 31/505* (2013.01); *A61K 31/513* (2013.01); *A61K 31/519* (2013.01); *A61K 31/535* (2013.01); *A61K 31/5383* (2013.01); *A61K 31/54* (2013.01); *A61K 31/542* (2013.01); *C07D 239/46* (2013.01); *C07D 239/48* (2013.01); *C07D 239/50* (2013.01); *C07D 498/04* (2013.01); *C07D 513/04* (2013.01); *Y10T 436/141111* (2015.01); *Y10T 436/143333* (2015.01)

(58) Field of Classification Search
CPC .. A61K 31/675; A61K 31/535; A61K 31/513; A61K 31/54; A61K 31/542; A61K 31/519; A61K 31/5383; A61K 31/4412; A61K 31/505; C07D 498/04; C07D 239/48; C07D 513/04; C07D 239/50; C07D 239/46
See application file for complete search history.

(56) References Cited

U.S. PATENT DOCUMENTS

| 4,587,342 A * | 5/1986 | Daluge ................ C07C 255/00 |
|  |  | 544/324 |
| 5,994,321 A | 11/1999 | Lewis et al. |
| 6,806,273 B1 | 10/2004 | Austin et al. |
| 2003/0134779 A1 * | 7/2003 | Diarra .................... A61K 38/40 |
|  |  | 514/2.5 |
| 2005/0054577 A1 | 3/2005 | Bueno |
| 2005/0197341 A1 | 9/2005 | Woolf |
| 2008/0004295 A1 | 1/2008 | Gore et al. |
| 2008/0269258 A1 | 10/2008 | Breaker et al. |

FOREIGN PATENT DOCUMENTS

| CA | 2132514 | 10/1993 |
| CA | 2435958 | 8/2002 |
| CA | 2499770 | 4/2004 |
| CA | 2649995 | 11/2007 |
| GB | 713652 | 8/1954 |
| WO | 2004027035 | 4/2004 |

(Continued)

OTHER PUBLICATIONS

Hong-Yun Li, MD; Yong-Ming Yao, MD; Zhi-Guo Shi, PhD; Ning Dong, BS; Yan Yu, BS; Lian-Rong Lu, BS; Zhi-Yong (C. Y.) Sheng, MD., Effect of 2,4-diamino-6-hydroxy-pyrimidine on postburn *Staphylococcus aureus* sepsis in rats, Crit Care Med 2002 vol. 30, No. 11, 2520-2527.*
Sahar I. Mostafa, Nick Hadjiliadis, Biologically active 2-thione-4,6-diamino-5-hydroxypyrimidine transition metal complexes, Transition Met Chem (2008) 33:529-534.*
Elżbieta Speina, Jarosław M. Cieśla, Maria-Anna Grąziewicz, Jacques Laval, Zygmunt Kazimierczuk and Barbara Tudek, Inhibition of DNA repair glycosylases by base analogs and tryptophan pyrolysate, Trp-P-1, Acta Biochimica Polonica, vol. 52 No. Jan. 2005, 167-178.*

(Continued)

*Primary Examiner* — Sarah Pihonak
*Assistant Examiner* — Jason Deck
(74) *Attorney, Agent, or Firm* — Julie Gauvreau

(57) ABSTRACT

The present invention includes novel compounds and pharmaceutically acceptable formulations of said compounds which exhibit antibiotic activity against microorganisms bearing a guanine riboswitch that controls the expression of the guaA gene, including organisms which are resistant to certain antibiotic families, and which are useful as antibacterial agents for treatment or prophylaxis of bacterial infections in animals or in humans, in particular but not limited to infections of the mammary gland, or their use as antiseptics, agents for sterilization or disinfection.

5 Claims, 10 Drawing Sheets

(56) References Cited

FOREIGN PATENT DOCUMENTS

| WO | WO 2006/055351 | 5/2006 |
|---|---|---|
| WO | 2007105023 | 9/2007 |
| WO | 2008086462 | 7/2008 |
| WO | 2008116223 | 9/2008 |
| WO | 2009015179 | 1/2009 |
| WO | 2010135504 | 11/2010 |

OTHER PUBLICATIONS

XP002691743, Database accession No. 2870982, Abstract & Liebigs Annalen Der Chemie, (1989): 409-412.
XP002691744, Database accession Nos. 816828, 987268, 4469521, 4496974, 4509706, Abstract & Synthesis, (1983): 837-839.
XP002691745, Database accession Nos. 977087, 987268, Abstract & J. Heterocyclic Chemistry (1971), 8: 503-505.
EP2440533, Extended European Search Report, dated Mar. 14, 2013.
EP2440533, Communication under 71(3), dated Apr. 15, 2015.
JP2012-514305, Office Action dated Jun. 3, 2014.
JP2012-514305, Certificate of patent, dated Jun. 5, 2015.
US20120122819, Restriction Requirement, dated Nov. 18, 2013.
US20120122819, Office Action, dated Apr. 9, 2014.
US20120122819, Office Action, dated Sep. 9, 2014.
Antonopoulou et al., "Immunomodulation in Sepsis: State of the Art and Future Perspective", (2011), 3(1): 117-128.
ISR PCT2010000868, dated Sep. 1, 2010, Socpra—Sciences et Genie S.E.C. et al.
Anderson et al., "Action of quinolones against Staphylococcus aureus topoisomerase IV: Basis for DNA cleavage enhancement", Biochem. (2000), 39:2726-2732.
Araki et al., "Molecular epidemiological studies of Staphylococcus aureus in urinary tract infection", J. Infect. Chemother, (2002), 8:168-174.
Barrick et al., "The distributions, mechanisms, and structures of metabolite-binding riboswitches", Genome Biol. (2007), 8, R239.
Batey et al., "Structure of a natural guanine-responsive riboswitch complexed with the metabolite hypoxanthine", Nature (2004), 432, 411-415.
Berge et al., "Pharmaceutical salts", J Pharm Sci. (1977), 66:1-19.
Blount et al., "Riboswitches as antibacterial drug targets", Nature Biotechnology (2006), 24 :1558-1564.
Coppins et al., "The intricate world of riboswitches", Curr Opin Microbiol. (2007), 10(2):176-181.
Corey, G.R. "Staphylococcus aureus bloodstream infections: Definitions and treatment" Clin. Infect. Dis. (2009), 48 (suppl. 4):S254-S259.
Garau et al., "Management of methicillin-resistant Staphylococcus aureus infections", Clin. Microbiol. Infect. (2009), 15:125-136.
Griffiths-Jones et al., "Rfam: annotating non-coding RNAs in complete genomes", Nucleic Acids Res. (2005), 33, D121-124.
Jones et al., "Multiple mutations conferring ciprofloxacin resistance in Staphylococcus aureus demonstrate long-term stability in an antibiotic-free environment", J. Antimicrob. Chemother (2000), 45:353-356.
Khanna, N. "Clindamycin-resistant Clostridium perfringens cellulitis", J. Tissue Viability (2008), 17:95-97.
Khanna, et al., "Methicillin resistant Staphylococcus aureus colonization in pigs and pig farmers", Vet. Microbiol. (2008), 128:298-303.
Knowles et al., "The bacterial ribosome, a promising focus for structure-based drug design" Current opinion in pharmacology (2002), 2:501-502.
Leffler et al., "Treatment of Clostridium difficile-associated disease", Gastroenterology (2009), 136:1899-1912.
Macke, et al., "RNAMotif, an RNA secondary structure definition and search algorithm", Nucleic Acids Res (2001), 29:4724-4735.

Mayer et al. "Oxygen concentration in milk of healthy and mastitic cows and implications of low oxygen tension for the killing of Staphylococcus aureus by bovine neutrophils", J. Dairy Res. (1988), 55:513.
Miller et al., "Structure-Based Design and Characterization of Novel Platforms for Ricin and Shiga Toxin Inhibition", J. Med. Chem. (2002), 45:90-98.
Moisan et al., "The Transcription of Virulence Factors in Staphylococcus aureus Small Colony Variants Isolated from Cystic Fibrosis Patients is Influenced by SigB", J. Bacteriol. (2006), 188:64-76.
Mulhbacher et al., "Ligand recognition determinants of guanine riboswitches", Nucleic Acids Res (2007), 35 :5568-5580.
Patel et al., "Synthesis and antimicrobial evaluation of guanylsulfonamides", Bioorg Med Chem Lett. (2007), 17:6610-6614.
Pruitt et al., "NCBI Reference Sequence (RefSeq): A curated nonredundant sequence database of genomes, transcripts, and proteins", Nucleic Acids Res. (2005), 33: D501-D504. doi: 10.1093/nar/gki011.
Russo et al., "Identification of two previously unrecognized genes (guaA and argC) important for uropathogenesis", Mol. Microbiol. (1996), 22:217-229.
Samant et al., "Nucleotic biosynthesis is crucial for growth of bacteria in human blood", PloS Pathogens (2008), 4(2): e37 (0001-0010).
Sears et al., "Management and treatment of staphylococcal mastitis", Vet. Clin. Food Anim. Pract. (2003), 19:171-185.
Sircar et al., "Inhibitors of human purine nucleoside phosphorylase. Synthesis, purine nucleoside phosphorylase inhibition, and T-cell cytotoxicity of 2,5-diaminothiazolo[5,4-d]pyrimidin-7(6H)-one and 2,5-diaminothiazolo[4,5-d]pyrimidin-7(6H)-one. Two thioisosteres of 8-aminoguanine", J Med Chem. Sep. 1986;29(9):1804-1806.
Songer et al., "Clostridial enteric infections in pigs", J. Vet. Diagn. Invest. (2005), 17:528-536.
Swann et al., "Role of postreplicative DNA mismatch repair in the cytotoxic action of thioguanine". Science (1996), 273(5278):1109-1111.
Talbot et al., "Antimicrobial Availability Task Force of the Infectious Diseases Society of America". Clin Infect Dis. (2006), 42:657-658.
Taylor et al., "Pyrrolo[3,2-d]pyrimidine folate analogues: "inverted" analogues of the cytotoxic agent LY231514", J Org Chem. (1995), 60:7947-7952.
Tiedeman et al., "Nucleotide Sequence of the guaA gene encoding GMP synthetase of Escherichia coli K12", J. Biol. Chem. (1985), 260:8676-8679.
Urleb et al., "The Synthesis and Transformations of 2-Ethoxycarbonyl-3-Isothiocyanatopyridine. Pyrido[3,2-d]pyrimidines and some Azolopyrido[3,2-d]pyrimidines" J. Het. Chem. (1990), 27:407-412.
Van Immerseel et al., "Clostridium perfringens in poultry: an emerging threat for animal and public health", Avian Pathol. (2004), 33:537-549.
Wilchelhaus et al., "Differential effect of rpoB mutations on antibacterial activities of rifampicin and KRM-1648 against Staphylococcus aureus", J. Antimicrob. Chemother. (2001), 47:153-156.
Brown, et al., "Evolutionary relationships of bacterial and archaeal glutamine synthetase genes", Abstract, (1994), J. Mol Evol. 38(6): 566-76.
Gabriel, "Amidoderivate des Pyrimidins", Chem. Ber. (1901), vol. 34(3): 3362-3366.
Gilbert et al., "Modified Pyrimidines Specifically Bind the Purine Riboswitch", J. Am. Chem. Soc., (2006), 128(44): 14214-14215.
Li et al., "Effect of 2,4-diamino-6-hydroxy-pyrimidine on postburn Staphylococcus aureus sepsis in rats", Crit. Care Med. (2002), 30(11): 2520-2527.
Hoshi et al., "Antitumor Activity of 2, 4, 5, and/or Substituted Derivatives of Pyrimidine", Pharmacometrics (1972), 6(5):1071-1073.
Koppel et al., "Potential Purine Antagonists. XIX. Synthesis of Some 9-Alkyl(aryl)-2-amino-6-substituted Purines and Related v-Triazolo(d)pyrimidines", J. Am. Chem. Soc., (1959), 81: 3046-3051.

(56) References Cited

OTHER PUBLICATIONS

Koppel et al., "Pyrimidines. I. Synthesis of Pyrimidinethiols", J. Org. Chem., (1961), 26: 792-803.
Masjost et al., "Structure based design, synthesis and in vitro evaluation of bisubstrate inhibitors for catechol O-methyltransferase (COMT)", Chemistry—A European Journal, (2000), 6(6): 971-982.
O'Brien et al., "Pyrimidines. VII. 2-Amino-4-(substituted anilino)pyrimidines", J. Org. Chem., (1961), 27(3): 1104-1107.
O'Brien et al., "Pyrimidines. IX. 4-and 5-(Substituted-anilino)pyrimidines", J. Med. Chem., (1962), 5(6): 1085-1103.
Roth et al., "Analogs of Pteroylglutamic Acid. V. 4-Alkylamino Derivatives", J. Am. Chem. Soc. (1950), 72(5): 1914-1918.
Traube, "Der Aufbau der Xanthinbasen aus der Cyanessigsaure. Synthese des Hypoxanthins and Adenins", Justus Liebigs Annalen Der Chemie, (1904), 331(1): 64-88.
XP002691739, Database accession No. 5871923, Abstract & J. Indian Chemical Society, (1965) 42:505-507.
XP002691740, Database accession No. 1660611, Abstract & J. Indian Chemical Society, (1987), 64: 612-615.
XP002691741, Database accession No. 128356, Abstract & J. Med. Chem.,(1986), 29(9): 1804-1806.
XP002691742, Database accession No. 3919951, Abstract & Liebigs Annalen Der Chemie, (1986): 780-784.

\* cited by examiner

S. aureus      E. coli

GUANINE RIBOSWITCH BINDING COMPOUNDS AND THEIR USE AS ANTIBIOTICS

CROSS REFERENCE TO RELATED APPLICATIONS

This application is a continuation of U.S. patent application Ser. No. 13/377,052 filed on Jan. 6, 2012, which is a National Entry Application of PCT application No. PCT/CA2010/000868 filed on Jun. 14, 2010 and published in English under PCT Article 21(2), which itself claims benefit of U.S. Provisional Applications Ser. No. 61/186,669, filed on Jun. 12, 2009 and No. 61/307,088 filed on Feb. 23, 2010. All documents above are incorporated herein in their entirety by reference.

FIELD OF THE INVENTION

The present invention relates to novel antimicrobial compounds. More specifically, the present invention is concerned with novel antimicrobial compounds which bind to a guanine riboswitch and inhibit the expression of the microbial gene guaA, methods of manufacturing same, disinfection, sterilization or antisepsis methods using same, and methods of treating or preventing microbial infections involving the administration of same.

BACKGROUND OF THE INVENTION

Bovine mastitis is the most frequently occurring and costly disease affecting dairy producers. The transmittable bacterium *Staphylococcus aureus* is the most common cause of bovine mastitis and current antibiotic therapies usually fail to eliminate the infection from dairy herds (Sears, P. M. and K. K. McCarthy, 2003).

Multiple drug resistance (MDR), partly due to the excessive and improper use of antibiotics both in human medicine and food animal production, is a growing problem that has come to the forefront particularly in the last decade. A major cause of this widespread multi-drug resistance is the fact that recent drug design has been largely based on a limited number of new chemical scaffolds, allowing pathogens to adapt and circumvent common antibiotic action mechanisms (Blount and Breaker, 2006). *Staphylococcus aureus* and *Clostridium difficile*, which are particularly prone to developing antibiotic resistance, are nosocomial pathogens of major importance responsible for a significant mortality rate in hospitals and increased health care costs (Talbot et al, 2006). Alternative antibacterial drugs targeting RNA, mainly based on a fortuitous interaction between an exogenous ligand and its RNA target, have recently been developed and may help alleviate the problem of MDR (Knowles et al, 2002). However, there remains a great need for the identification of novel antimicrobial targets and compounds.

Bacterial riboswitches as a mechanism for regulating gene expression are known in the art. Riboswitches are segments of the 5'-untranslated region of certain mRNA molecules that, upon recognition of specific ligands, modify the expression of one or more proteins encoded in the message. Ligand-binding results in structural changes in the riboswitch that affect the ability of the mRNA molecule to be properly transcribed or translated. Thus riboswitches can function as RNA sensors, allowing control of gene expression at the mRNA level. The best-characterized riboswitches contain an aptamer region that is involved in ligand binding and an expression platform that is responsible for bringing about changes in gene expression (Coppins et al., 2007).

The scientific literature suggests that all bacterial riboswitches indiscriminately represent molecular antimicrobial targets. However, in order to develop novel specific antimicrobial therapies that will avoid contributing to widespread MDR, it would be highly desirable to identify riboswitches that are therapeutically selective, i.e., riboswitches that do not represent antimicrobial targets in all microbial species or commensal microorganisms that bear similar switches but on the contrary, riboswitches that have specific properties that only appear in the targeted pathogens.

Guanine riboswitches represent a subclass of riboswitches that are known in the art (Barrick and Breaker, 2007; Batey et al, 2004; Mulhbacher and Lafontaine, 2007). Application WO 2006/55351 teaches that the guanine riboswitch, in the presence of the guanine ligand, inhibits the expression of the genes xpt and pbuX in the non-pathogenic bacteria *Bacillus subtilis*. Some of the guanine analogs proposed in application WO 2006/55351 as potential therapeutic agents were reported to have non-specific antibacterial activities in vitro against a broad selection of pathogenic and non-pathogenic bacteria including the non-pathogenic *Bacillus subtilis*. Furthermore, later studies from the same investigators reported that these two genes (xpt and pbuX), assumed to be controlled by the guanine riboswitch, were expected to be non essential for the survival or virulence of *Staphylococcus aureus* (Blount and Breaker, 2006). It is well known in the field that genes (and their products) that are essential for the survival or virulence of a microbial pathogen represent ideal targets to obtain quick microbial killing, while avoiding the development of microbial resistance arising from mutations inactivating non-essential anti-microbial targets. The teachings of WO 2006/55351 and of Blount and Breaker (2006) thus suggested that the guanine riboswitch was not a desirable target for selective antibacterial intervention against the pathogen *S. aureus* in vivo.

Hence in this field of research and therapeutic applications, it would be highly desirable to identify microbial pathogens having essential survival or virulence gene(s) under control of a riboswitch. It would also be highly desirable to identify antimicrobial compounds that specifically bind to these riboswitches and selectively inhibit the expression of the gene(s) essential for the survival or virulence of specific pathogens in vivo. Such compounds would allow selective treatment of pathogens affecting animals and humans. It would also be highly desirable to identify compounds that are sufficiently distinct from the natural riboswitch ligand to avoid transformation of the compound by the host or microbial flora (for example by ribosylation) and to prevent potential broad and non-specific bacterial growth inhibition or toxicity to the mammalian host.

The present invention seeks to meet these and other needs.

The present description refers to a number of documents, the content of which is herein incorporated by reference in their entirety.

SUMMARY OF THE INVENTION

The present invention discloses that expression of the gene guaA (Tiedeman et al, 1985) encoding GMP synthetase (glutamine aminotransferase), which catalyses the synthesis of GMP (guanosine-5'-monophosphate) is under the control of a guanine riboswitch and is needed for survival or virulence in some relevant environments (e.g., during infection of a mammalian host) for specific pathogens. The present invention also presents antibiotic-like compounds with antimicrobial activity against such pathogens. Furthermore, such compounds cannot be modified by ribosylation to prevent incorporation into cellular nucleosides, nucleotides or nucleic acids, and thus prevent broad, non-specific toxicity for bacterial species not targeted by the compound and for the mammalian or animal host in which the present compounds are used for therapeutic intervention.

More specifically, in accordance with an aspect of the present invention, there is provided a compound of the general formula 1.0,

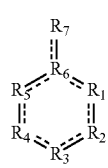

(1.0)

wherein, when said compound is bound to a guanine riboswitch, R3 may serve as a hydrogen bond acceptor but cannot be ribosylated; wherein ____ represents a single or double bond; wherein R3 is —N═, —S—, —CH═ or —O—; wherein R6 is a carbon atom; wherein R1, R2, R4 or R5 are identical or different and are independently —NR8-, —CHR8-, ═CR8-, —C(═O)— or —C(═NR8)-; wherein R8 is —H, —NH$_2$, —OH, —SH, a halide, fluorine, chlorine, bromine, iodine, —CO$_2$H, —CO$_2$-alkyl, —CO$_2$-aryl, —C(O)NH$_2$, —CH$_3$, —POOH, —SO$_2$alkyl, —SO$_2$aryl, —SH, substituted or unsubstituted alkyl, substituted or unsubstituted alkoxy, substituted or unsubstituted aryl, substituted or unsubstituted aryloxy, substituted or unsubstituted benzyloxy, substituted or unsubstituted —NHalkyl, substituted or unsubstituted —NHalkoxy, substituted or unsubstituted —NHC(O)alkyl, substituted or unsubstituted —NHCO$_2$alkyl, substituted or unsubstituted —NH—NHalkyl, substituted or unsubstituted —NH—NHalkoxy, substituted or unsubstituted —NH—SO$_2$alkyl, —NHC(O)NH$_2$, —NH—NH$_2$, —NH—SO$_2$—R9, —NHCO$_2$CH$_2$—R9, —NH—OR9, —NH$_2$—R9, —NH—NH—R9, —NHR9, —NH—CH$_2$—R9, or —NH—NH—CH$_2$—R9, wherein R9 is:

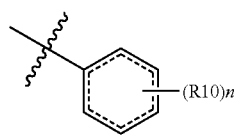

wherein n is an integer from 1 to 5; wherein R10 is —H, —NH$_2$, —OH, alkoxy, —N-morpholino, a halide, fluorine, chlorine, bromine or iodine; wherein, R7 is ═O, —OH, —SH, —NH$_2$, —CO$_2$H, —CO$_2$-alkyl, —CO$_2$-aryl, —C(O)NH$_2$, -alkoxy, -aryloxy, -benzyloxy, a halide, fluorine, chlorine, bromine, iodine, —NHalkyl, —NHalkoxy, —NHC(O)alkyl, —NHCO$_2$alkyl, ═NR8, ═NR9, —NHCO$_2$CH$_2$—R9, —NHC(O)NH$_2$, —NH—NH$_2$, —NH—NHalkyl, —NH—NHalkoxy, —SO$_2$alkyl, —SO$_2$aryl, —NH—SO$_2$alkyl, —NH—SO$_2$—R9, —NH—OR9, —NH$_2$—R9, —NH—NH—R9, —NH—NH—CH$_2$—R9, or —NH—CH$_2$—R9, wherein R8 and R9 are as defined above, with the proviso that the compound is not: 4-hydroxy-2,5,6-triaminopyrimidine (1.01); 2,4-diamino-6-hydroxypyrimidine (1.13); or 4,5-diamino-6-hydroxy-2-mercaptopyrimidine (1.16).

It is well understood by those skilled in the art that heterocyclic compounds such as the compounds of the present invention can exist under different tautomeric forms, each tautomeric form being described using a specific formula and a specific name. Herein, the use of the name of one tautomeric form of a compound is meant to refer to and encompass all other tautomeric forms of the same compound. For example, as used herein, the terms "4-hydroxy-2,5,6-triaminopyrimidine" and "formula 1.01" are meant to refer to both "4-hydroxy-2,5,6-triaminopyrimidine" and "2,5,6-triaminopyrimidine-4-one".

As used herein, the terms "4,5-diamino-6-hydroxy-2-mercaptopyrimidine" or "formula 1.16" are meant to refer to both "4,5-diamino-6-hydroxy-2-mercaptopyrimidine" and "5,6-diamino-2-mercaptopyrimidine-4-one".

As used herein, the terms "2,4-diamino-6-hydroxypyrimidine" or "formula 1.13" are meant to refer to both "2,4-diamino-6-hydroxypyrimidine" and "2,6-diaminopyrimidine-4-one".

As used herein, the terms "9-oxoguanine" or "formula 2.02" are meant to refer to both "9-oxoguanine" and "5-Amino-6H-oxazolo[5,4-d]pyrimidin-7-one".

In a specific embodiment of the composition of the general formula 1.0, (i) R1 is —NH—; (ii) R2 is —C(NH$_2$)═ or ═C(SH)—; (iii) R3 is —N═; (iv) R4 is ═CNH$_2$—; R5 is —CH═ or —C(NH$_2$)═; R6 is —C═; R7 is ═NH or ═O; or any combination of (i) to (vii).

In accordance with another aspect of the present invention, there is provided a compound of the general formula 2.0,

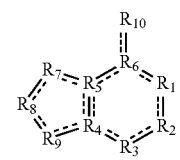

(2.0)

wherein, when said compound is bound to a guanine riboswitch, R9 may serve as a hydrogen bond donor but cannot be ribosylated; wherein ____ represents a single or double bond; wherein R3 is —N═, —S—, or —O—; wherein R1 or R2 are identical or different and are independently —NR11-, —CHR11-, ═CR11-, —C(═O)— or —C(═NR11)-; wherein R11 is —H, —NH$_2$, —OH, —SH, —CO$_2$H, —CO$_2$-alkyl, —CO$_2$-aryl, —C(O)NH$_2$, —CH$_3$, —POOH, —SO$_2$alkyl, —SO$_2$aryl, —SH, substituted or unsubstituted alkyl, substituted or unsubstituted alkoxy, substituted or unsubstituted aryl, substituted or unsubstituted aryloxy, substituted or unsubstituted benzyloxy, substituted or unsubstituted —NHalkyl, substituted or unsubstituted —NHalkoxy, substituted or unsubstituted —NHC(O)alkyl, substituted or unsubstituted —NHCO$_2$alkyl, substituted or unsubstituted —NH—NHalkyl, substituted or unsubstituted —NH—NHalkoxy, substituted or unsubstituted —NH—SO$_2$alkyl, —NHC(O)NH$_2$, —NH—NH$_2$, —NH—SO$_2$—R12, —NHCO$_2$CH$_2$—R12, —NH—OR12, —NH$_2$—R12, —NH—NH—R12, —NHR12, —NH—CH$_2$—R12, or —NH—NH—CH$_2$—R12;

wherein R12 is:

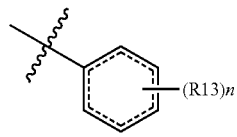

wherein n is in integer from 1 to 5; wherein R13 is at least one of —H, —NH$_2$, —OH, alkoxy, —N-morpholino, a halide, fluorine, chlorine, bromine, iodine; wherein R4, R5 and R6 are carbon atoms; wherein R7 is —N═, —NH—, —CH$_2$—, —O— or —S—; wherein R8 is —CH$_2$, —O—, —S—, —CHR13- or —CR13═, wherein R13 is as defined above; wherein R9 is —O—, —S—, or —P(OOH)—, —N═; wherein R10 is ═O, —OH, —SH, —NH$_2$, —CO$_2$H, —CO$_2$-alkyl, —CO$_2$-aryl, —C(O)NH$_2$, -alkoxy, -aryloxy, -benzyloxy, a halide, fluorine, chlorine, bromine, iodine, —NHalkyl, —NHalkoxy, —NHC(O)alkyl, —NHCO$_2$alkyl, ═NR11, ═NR12, —NHCO$_2$CH$_2$—R12, —NHC(O)NH$_2$, —NH—NH$_2$, —NH—NHalkyl, —NH—NHalkoxy, —SO$_2$alkyl, —SO$_2$aryl, —NH—SO$_2$alkyl, —NH—SO$_2$—R12, —NH—OR12, —NH—R12, —NH—NH—R12, —NH—NH—CH$_2$—R12, or —NH—CH$_2$—R12; wherein R11 and R12 are as defined above, with the proviso that the compound is not: guanine, hypoxanthine, xanthine or 5-amino-2-chloro-2,3-dihydrothiazolo[4,5]pyrimidine-7-(6H)-one (2.17).

In accordance with another aspect of the present invention, there is provided a compound of the general formula 3.0,

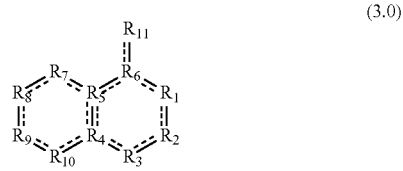

wherein, when the compound is bound to a guanine riboswitch, R10 may serve as a hydrogen bond donor but cannot be ribosylated; wherein ---- represents a single or double bond; wherein R3 is —N═, —S—, or —O—; wherein R10 is —N═, —CH$_2$—, —O—, —S—, or —P(OOH)—; wherein R1, R2 and R9 are identical or different and are independently —NR12-, —CHR12-, ═CR12-, —C(═O)— or —C(═NR12)-; wherein R12 is —H, —NH$_2$, —OH, —SH, —CO$_2$H, —CO$_2$-alkyl, —CO$_2$-aryl, —C(O)NH$_2$, —CH$_3$, —POOH, —SO$_2$alkyl, —SO$_2$aryl, —SH, substituted or unsubstituted alkyl, substituted or unsubstituted alkoxy, substituted or unsubstituted aryl, substituted or unsubstituted aryloxy, substituted or unsubstituted benzyloxy, substituted or unsubstituted —NHalkyl, substituted or unsubstituted —NHalkoxy, substituted or unsubstituted —NHC(O)alkyl, substituted or unsubstituted —NHCO$_2$alkyl, substituted or unsubstituted —NH—NHalkyl, substituted or unsubstituted —NH—NHalkoxy, substituted or unsubstituted —NH—SO$_2$alkyl, —NHC(O)NH$_2$, —NH—NH$_2$, —NH—SO$_2$—R13, —NHCO$_2$CH$_2$—R13, —NH—OR13, —N+H2-R13, —NH—NH—R13, —NHR13, —NH—CH$_2$—R13, or —NH—NH—CH$_2$—R13; wherein R13 is:

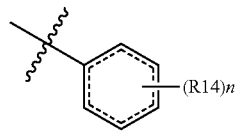

wherein n is an integer from 1 to 5; wherein R14 is —H, —NH$_2$, —OH, alkoxy, —N-morpholino, a halide, fluorine, chlorine, bromine, or iodine; wherein R4, R5 and R6 are carbon atoms; wherein R7 and R8 are identical or different and are independently —CH═N—, —CH$_2$—O—, CH$_2$—S—, or CH$_2$SO$_2$—; wherein R11 is ═O, —OH, —SH, —NH$_2$, —CO$_2$H, —CO$_2$-alkyl, —CO$_2$-aryl, —C(O)NH$_2$, -alkoxy, -aryloxy, -benzyloxy, a halide, fluorine, chlorine, bromine, iodine, —NHalkyl, —NHalkoxy, —NHC(O)alkyl, —NHCO$_2$alkyl, ═NR12, ═NR13, —NHCO$_2$CH$_2$—R13, —NHC(O)NH$_2$, —NH—NH$_2$, —NH—NHalkyl, —NH—NHalkoxy, —SO$_2$alkyl, —SO$_2$aryl, —NH—SO$_2$alkyl, —NH—SO$_2$—R13, —NH—OR13, —NH—R13, —NH—NH—R13, —NH—NH—CH$_2$—R13, or —NH—CH$_2$—R13; and wherein R12 and R13 are as defined above.

In accordance with an aspect of the present invention, there is provided a compound of the general formula (2.0a),

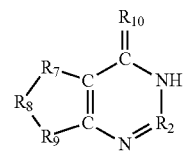

wherein R2, R7, R8, R9 and R10 are as defined for formula 2.0 above.

In a specific embodiment of the compound of the present invention, there is provided a compound of the general formula (2.0), wherein: (i) R1 is —NH—; (ii) R2 is ═CNH$_2$—; (iii) R3 is —N═; (iv) R7 is —N═ or —S—; (v) R8 is —CR13═; (vi) R9 is —O— or —N═; (vii) R10 is ═O or ═NH; or (viii) any combination of (i) to (vii).

In another specific embodiment of the compound of formula 2.0a of the present invention, R2 is ═CNH$_2$, in another specific embodiment, R7 is —N═ or —S—, in another specific embodiment, R8 is —CR13═, in another specific embodiment, R9 is —O— or —N═, in another specific embodiment, R10 is ═O or ═NH.

In accordance with an aspect of the present invention, there is provided a compound of the general formula 3.0a,

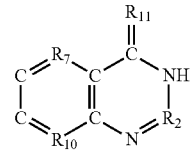

wherein, R2, R7, R10 and R11 are as defined as defined for formula 3.0 above.

In accordance with another aspect of the present invention, there is provided a compound of the general formula 1.0a,

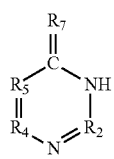
(1.0a)

wherein R2 and R7 are as defined for formula 1.0 above and wherein R5 is —CH= or —C(NH$_2$)= while R4 is —C(NH$_2$)=.

In a specific embodiment of the compound of the general formula 1.0a, R7 is =O or =NH. In a specific embodiment of the compound of the general formula 1.0a, R2 is —C(NH$_2$)= or —C(SH)=.

In accordance with another aspect of the present invention, there is provided the compound defined above, for (a) preventing or treating a microbial infection in a subject, wherein said microbial infection is caused by a pathogen bearing a guanine riboswitch that controls the expression of guaA; or (b) the disinfection, sterilization and/or antisepsis of an object from a pathogen bearing a guanine riboswitch that controls the expression of guaA; or (c) treating a multi-drug resistant bacteria or preventing the development of a multi-drug resistant bacteria, wherein the bacteria bears a guanine riboswitch that controls the expression of guaA.

In accordance with another aspect of the present invention, there is provided a composition comprising a compound of the general formula 1.0,

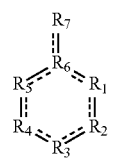

wherein, when said compound is bound to a guanine riboswitch, R3 may serve as a hydrogen bond acceptor but cannot be ribosylated; wherein ---- represents a single or double bond; wherein R3 is —N=, —S—, —CH= or —O—; wherein R6 is a carbon atom; wherein R1, R2, R4 or R5 are identical or different and are independently —NR8-, —CHR8-, =CR8-, —C(=O)— or —C(=NR8)-; wherein R8 is —H, —NH$_2$, —OH, —SH, a halide, fluorine, chlorine, bromine, iodine, —CO$_2$H, —CO$_2$-alkyl, —CO$_2$-aryl, —C(O)NH$_2$, —CH$_3$, —POOH, —SO$_2$alkyl, —SO$_2$aryl, —SH, substituted or unsubstituted alkyl, substituted or unsubstituted alkoxy, substituted or unsubstituted aryl, substituted or unsubstituted aryloxy, substituted or unsubstituted benzyloxy, substituted or unsubstituted —NHalkyl, substituted or unsubstituted —NHalkoxy, substituted or unsubstituted —NHC(O)alkyl, substituted or unsubstituted —NHCO$_2$alkyl, substituted or unsubstituted —NH—NHalkyl, substituted or unsubstituted —NH—NHalkoxy, substituted or unsubstituted —NH—SO$_2$alkyl, —NHC(O)NH$_2$, —NH—NH$_2$, —NH—SO$_2$—R9, —NHCO$_2$CH$_2$—R9, —NH—OR9, —NH$_2$—R9, —NH—NH—R9, —NHR9, —NH—CH$_2$—R9, or —NH—NH—CH$_2$—R9, wherein R9 is:

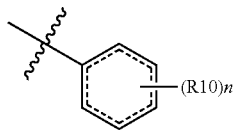

wherein n is an integer from 1 to 5; wherein R10 is —H, —NH$_2$, —OH, alkoxy, —N-morpholino, a halide, fluorine, chlorine, bromine or iodine; wherein, R7 is =O, —OH, —SH, —NH$_2$, —CO$_2$H, —CO$_2$-alkyl, —CO$_2$-aryl, —C(O)NH$_2$, -alkoxy, -aryloxy, -benzyloxy, a halide, fluorine, chlorine, bromine, iodine, —NHalkyl, —NHalkoxy, —NHC(O)alkyl, —NHCO$_2$alkyl, =NR8, =NR9, —NHCO$_2$CH$_2$—R9, —NHC(O)NH$_2$, —NH—NH$_2$, —NH—NHalkyl, —NH—NHalkoxy, —SO$_2$alkyl, —SO$_2$aryl, —NH—SO$_2$alkyl, —NH—SO$_2$—R9, —NH—OR9, —NH—R9, —NH—NH—R9, —NH—NH—CH$_2$—R9, or —NH—CH$_2$—R9, wherein R8 and R9 are as defined above, and (a) an antibiotic; (b) an antiseptic; (c) a disinfectant; (d) a diluent; (e) an excipient; (f) a pharmaceutically acceptable carrier; or any combination of (a)-(f).

In accordance with another aspect of the present invention, there is provided a composition comprising a compound of the general formula 2.0,

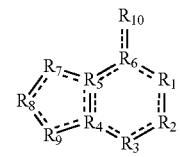

wherein, when said compound is bound to a guanine riboswitch, R9 may serve as a hydrogen bond donor but cannot be ribosylated; wherein ---- represents a single or double bond; wherein R3 is —N=, —S—, or —O—; wherein R1 or R2 are identical or different and are independently —NR11-, —CHR11-, =CR11-, —C(=O)— or —C(=NR11)-; wherein R11 is —H, —NH$_2$, —OH, —SH, —CO$_2$H, —CO$_2$-alkyl, —CO$_2$-aryl, —C(O)NH$_2$, —CH$_3$, —POOH, —SO$_2$alkyl, —SO$_2$aryl, —SH, substituted or unsubstituted alkyl, substituted or unsubstituted alkoxy, substituted or unsubstituted aryl, substituted or unsubstituted aryloxy, substituted or unsubstituted benzyloxy, substituted or unsubstituted —NHalkyl, substituted or unsubstituted —NHalkoxy, substituted or unsubstituted —NHC(O)alkyl, substituted or unsubstituted —NHCO$_2$alkyl, substituted or unsubstituted —NH—NHalkyl, substituted or unsubstituted —NH—NHalkoxy, substituted or unsubstituted —NH—SO$_2$alkyl, —NHC(O)NH$_2$, —NH—NH$_2$, —NH—SO$_2$—R12, —NHCO$_2$CH$_2$—R12, —NH—OR12, —NH$_2$—R12, —NH—NH—R12, —NHR12, —NH—CH$_2$—R12, or —NH—NH—CH$_2$—R12;

wherein R12 is:

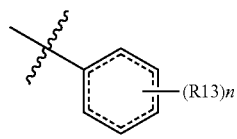

wherein n is in integer from 1 to 5; wherein R13 is at least one of —H, —NH$_2$, —OH, alkoxy, —N-morpholino, a halide, fluorine, chlorine, bromine, iodine; wherein R4, R5 and R6 are carbon atoms; wherein R7 is —N═, —NH—, —CH$_2$—, —O— or —S—; wherein R8 is —CH$_2$, —O—, —S—, —CHR13- or —CR13═, wherein R13 is as defined above; wherein R9 is —O—, —S—, or —P(OOH)—, —N═; wherein R10 is ═O, —OH, —SH, —NH$_2$, —CO$_2$H, —CO$_2$-alkyl, —CO$_2$-aryl, —C(O)NH$_2$, -alkoxy, -aryloxy, -benzyloxy, a halide, fluorine, chlorine, bromine, iodine, —NHalkyl, —NHalkoxy, —NHC(O)alkyl, —NHCO$_2$alkyl, ═NR11, ═NR12, —NHCO$_2$CH$_2$—R12, —NHC(O)NH$_2$, —NH—NH$_2$, —NH—NHalkyl, —NH—NHalkoxy, —SO$_2$alkyl, —SO$_2$aryl, —NH—SO$_2$alkyl, —NH—SO$_2$—R12, —NH—OR12, —NH—R12, —NH—NH—R12, —NH—NH—CH$_2$—R12, or —NH—CH$_2$—R12; wherein R11 and R12 are as defined above, and an (a) antibiotic; (b) an antiseptic; (c) a disinfectant; (d) a diluent; (e) an excipient; (f) a pharmaceutically acceptable carrier; or any combination of (a)-(f).

In accordance with another aspect of the present invention, there is provided a composition comprising a compound of the general formula 3.0,

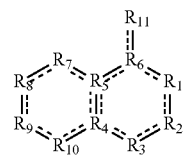

wherein, when the compound is bound to a guanine riboswitch, R10 may serve as a hydrogen bond donor but cannot be ribosylated; wherein ---- represents a single or double bond; wherein R3 is —N═, —S—, or —O—; wherein R10 is —N═, —CH$_2$—, —O—, —S—, or —P(OOH)—; wherein R1, R2 and R9 are identical or different and are independently —NR12-, —CHR12-, ═CR12-, —C(═O)— or —C(═NR12)-; wherein R12 is —H, —NH$_2$, —OH, —SH, —CO$_2$H, —CO$_2$-alkyl, —CO$_2$-aryl, —C(O)NH$_2$, —CH$_3$, —POOH, —SO$_2$alkyl, —SO$_2$aryl, —SH, substituted or unsubstituted alkyl, substituted or unsubstituted alkoxy, substituted or unsubstituted aryl, substituted or unsubstituted aryloxy, substituted or unsubstituted benzyloxy, substituted or unsubstituted —NHalkyl, substituted or unsubstituted —NHalkoxy, substituted or unsubstituted —NHC(O)alkyl, substituted or unsubstituted —NHCO$_2$alkyl, substituted or unsubstituted —NH—NHalkyl, substituted or unsubstituted —NH—NHalkoxy, substituted or unsubstituted —NH—SO$_2$alkyl, —NHC(O)NH$_2$, —NH—NH$_2$, —NH—SO$_2$—R13, —NHCO$_2$CH$_2$—R13, —NH—OR13, —N+H2-R13, —NH—NH—R13, —NHR13, —NH—CH$_2$—R13, or —NH—NH—CH$_2$—R13;

wherein R13 is:

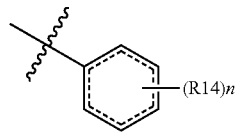

wherein n is an integer from 1 to 5; wherein R14 is —H, —NH$_2$, —OH, alkoxy, —N-morpholino, a halide, fluorine, chlorine, bromine, or iodine; wherein R4, R5 and R6 are carbon atoms; wherein R7 and R8 are identical or different and are independently —CH═N—, —CH$_2$—O—, CH$_2$—S—, or CH$_2$SO$_2$—; wherein R11 is ═O, —OH, —SH, —NH$_2$, —CO$_2$H, —CO$_2$-alkyl, —CO$_2$-aryl, —C(O)NH$_2$, -alkoxy, -aryloxy, -benzyloxy, a halideo, fluorine, chlorine, bromine, iodine, —NHalkyl, —NHalkoxy, —NHC(O)alkyl, —NHCO$_2$alkyl, ═NR12, ═NR13, —NHCO$_2$CH$_2$—R13, —NHC(O)NH$_2$, —NH—NH$_2$, —NH—NHalkyl, —NH—NHalkoxy, —SO$_2$alkyl, —SO$_2$aryl, —NH—SO$_2$alkyl, —NH—SO$_2$—R13, —NH—OR13, —NH—R13, —NH—NH—R13, —NH—NH—CH$_2$—R13, or —NH—CH$_2$—R13; and wherein R12 and R13 are as defined above, and (a) an antibiotic; (b) an antiseptic; (c) a disinfectant; (d) a diluent; (e) an excipient; (f) a pharmaceutically acceptable carrier; or any combination of (a)-(f).

In a specific embodiment of the composition of the present invention, the compound is of the general formula,

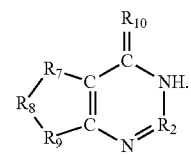

In another specific embodiment of the composition of the present invention, the compound is of the general formula,

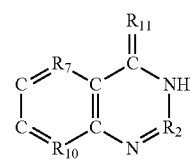

In another specific embodiment of the composition of the present invention, the compound is of the general formula,

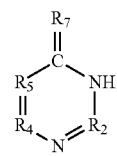

wherein R5 and R4 are independently —CH═ or —C(NH$_2$)═.

In accordance with another aspect of the present invention, there is provided a composition comprising (i) 4-hydroxy-2,5,6-triaminopyrimidine (formula 1.01); (ii) 4,5-diamino-6-hydroxy-2-mercaptopyrimidine (formula 1.16); (iii) 2,4-diamino-6-hydroxypyrimidine (formula 1.13); or (iv) 5-amino-2-chloro-2,3-dihydrothiazolo[4,5]pyrimidine-7-(6H)-one (2.17); and (a) an antibiotic; (b) an antiseptic; (c) a disinfectant; (d) a pharmaceutically acceptable carrier; or (e) any combination of (a)-(d).

In accordance with another aspect of the present invention, the composition defined above is for (a) preventing or treating a microbial infection in a subject, wherein said microbial infection is caused by a pathogen bearing a guanine riboswitch that controls the expression of guaA; or (b) the disinfection, sterilization and/or antisepsis of an object from a pathogen bearing a guanine riboswitch that controls the expression of guaA; or (c) treating a multi-drug resistant bacteria or preventing the development of a multi-drug resistant bacteria, wherein the bacteria bears a guanine riboswitch that controls the expression of guaA.

In another specific embodiment, said composition is a pharmaceutical composition.

In accordance with another aspect of the present invention there is provided a method of preventing or treating a microbial infection in a subject, said method comprising administering to said subject a therapeutically effective amount of a non ribosylable ligand of a guanine riboswitch, wherein said microbial infection is caused by a pathogen bearing the guanine riboswitch, and wherein the guanine riboswitch controls the expression of guaA.

In accordance with another aspect of the present invention, there is provided a method of preventing or treating a microbial infection in a subject, said method comprising administering to said subject a therapeutically effective amount of the compound defined above or of the above-mentioned composition, wherein said microbial infection is caused by a pathogen bearing a guanine riboswitch that controls the expression of guaA.

In a specific embodiment of the method, said non ribosylable ligand of a guanine riboswitch is (i) the compound defined above; (ii) 4-hydroxy-2,5,6-triaminopyrimidine (formula 1.01); (iii) 4,5-diamino-6-hydroxy-2-mercaptopyrimidine (formula 1.16); (iv) 2,4-diamino-6-hydroxypyrimidine (formula 1.13); or (v) 5-amino-2-chloro-2,3-dihydrothiazolo[4,5]pyrimidine-7-(6H)-one (2.17).

In a specific embodiment of the method of the present invention, said subject is an animal (e.g., cattle such as cow; goat, ewe, ass, horse, pig; cat; dog; etc.). In another specific embodiment, said subject is a cow. In another specific embodiment, said subject is a human. In another specific embodiment, said pathogen is a bacteria belonging to the genus *Staphylococcus* or *Clostridium*. In another specific embodiment, said bacteria is *Staphylococcus aureus*, methicillin-resistant *Staphylococcus aureus, Staphylococcus epidermidis, Staphylococcus haemolyticus, Clostridium botulinum* or *Clostridium difficile*. In another specific embodiment, said infection is a mammary gland infection.

In accordance with another aspect of the present invention, there is provided a use of a therapeutically effective amount of a non ribosylable ligand of a guanine riboswitch, for preventing or treating a microbial infection in a subject, wherein said microbial infection is caused by a pathogen bearing the guanine riboswitch, and wherein the guanine riboswitch controls the expression of guaA.

In accordance with another aspect of the present invention, there is provided a use of a therapeutically effective amount of a non ribosylable ligand of a guanine riboswitch, for the manufacture of a medicament for preventing or treating a microbial infection in a subject, wherein said microbial infection is caused by a pathogen bearing the guanine riboswitch, and wherein the guanine riboswitch controls the expression of guaA.

In accordance with another aspect of the present invention, there is provided a use of the compound defined above or of the above-mentioned composition, for preventing or treating a microbial infection in a subject, wherein said microbial infection is caused by a pathogen bearing the guanine riboswitch, and wherein the guanine riboswitch controls the expression of guaA.

In accordance with another aspect of the present invention, there is provided a use of the compound defined above or of the above-mentioned composition, for the manufacture of a medicament for preventing or treating a microbial infection in a subject, wherein said microbial infection is caused by a pathogen bearing the guanine riboswitch, and wherein the guanine riboswitch controls the expression of guaA.

In a specific embodiment of said uses, said non ribosylable ligand of a guanine riboswitch is (i) the compound defined above; (ii) 4-hydroxy-2,5,6-triaminopyrimidine (formula 1.01); (iii) 4,5-diamino-6-hydroxy-2-mercaptopyrimidine (formula 1.16); (iv) 2,4-diamino-6-hydroxypyrimidine (formula 1.13); or (v) 5-amino-2-chloro-2,3-dihydrothiazolo[4,5]pyrimidine-7-(6H)-one (2.17).

In a specific embodiment of the use of the present invention, said subject is an animal (e.g., cattle such as cow; goat, ewe, ass, horse, pig; cat; dog; etc.). In another specific embodiment, said subject is a cow. In another specific embodiment said subject is a human. In another specific embodiment, said pathogen is a bacteria belonging to the genus *Staphylococcus* or *Clostridium*. In another specific embodiment, said bacteria is *Staphylococcus aureus*, methicillin-resistant *Staphylococcus aureus, Staphylococcus epidermidis, Staphylococcus haemolyticus, Clostridium botulinum* or *Clostridium difficile*. In another specific embodiment, said infection is a mammary gland infection.

In accordance with another aspect of the present invention, there is provided a method of disinfecting and/or sterilizing an object of a pathogen, said method comprising applying an effective amount of a non ribosylable ligand of a guanine riboswitch to said object, wherein said pathogen bears a guanine riboswitch that controls the expression of guaA.

In accordance with another aspect of the present invention, there is provided a method of disinfecting and/or sterilizing an object of a pathogen, said method comprising applying an effective amount of the compound defined above or of the above-mentioned composition to said object, wherein said pathogen bears a guanine riboswitch that controls the expression of guaA.

In a specific embodiment of the method of the present invention, said non ribosylable ligand of a guanine riboswitch is (i) the compound of defined above; (ii) 4-hydroxy-2,5,6-triaminopyrimidine (formula 1.01); (iii) 4,5-diamino-6-hydroxy-2-mercaptopyrimidine (formula 1.16); (iv) 2,4-diamino-6-hydroxypyrimidine (formula 1.13); or (v) 5-amino-2-chloro-2,3-dihydrothiazolo[4,5]pyrimidine-7-(6H)-one (2.17).

In a specific embodiment of the methods, said object is an animal or milk.

In accordance with another aspect of the present invention, there is provided a use of an effective amount of a non ribosylable ligand of a guanine riboswitch for the disinfection, sterilization and/or antisepsis of an object from a pathogen, said pathogen bearing a guanine riboswitch that controls the expression of guaA.

In accordance with another aspect of the present invention, there is provided a use of the compound defined above or of the above-mentioned composition for the disinfection, sterilization and/or antisepsis of an object from a pathogen bearing a guanine riboswitch that controls the expression of guaA.

In a specific embodiment of the use, said non ribosylable ligand of a guanine riboswitch is (i) the compound defined above; (ii) 4-hydroxy-2,5,6-triaminopyrimidine (formula 1.01); (iii) 4,5-diamino-6-hydroxy-2-mercaptopyrimidine (formula 1.16); (iv) 2,4-diamino-6-hydroxypyrimidine (formula 1.13); or (v) 5-amino-2-chloro-2,3-dihydrothiazolo[4,5]pyrimidine-7-(6H)-one (2.17).

In a specific embodiment of the uses, said object is an animal or milk.

In accordance with another aspect of the present invention, there is provided a method of selecting a pathogen treatable by a non ribosylable ligand of a guanine riboswitch, or the compound defined above, or the above-mentioned composition, said method comprising determining whether said pathogen bears a guanine riboswitch that controls the expression of guaA.

In a specific embodiment of the method, the method is method of selecting a pathogen treatable by (i) the compound defined above; (ii) 4-hydroxy-2,5,6-triaminopyrimidine (formula 1.01); (iii) 4,5-diamino-6-hydroxy-2-mercaptopyrimidine (formula 1.16); (iv) 2,4-diamino-6-hydroxypyrimidine (formula 1.13); (v) 5-amino-2-chloro-2,3-dihydrothiazolo[4,5]pyrimidine-7-(6H)-one (2.17); or (vi) the above-mentioned composition, said method comprising determining whether said pathogen bears a guanine riboswitch that controls the expression of guaA.

In accordance with another aspect of the present invention, there is provided a method of identifying a compound for treating or preventing a microbial infection caused by a pathogen bearing a guanine riboswitch that controls the expression of guaA, said method comprising contacting said pathogen with a candidate compound and determining the effect of said compound of the growth or survival of said pathogen, wherein a decrease in the growth or survival of said pathogen in the presence as compared to in the absence of said candidate compound is an indication that said compound is suitable for treating or preventing said microbial infection.

In accordance with another aspect of the present invention, there is provided a method of identifying a compound for preventing or treating a microbial infection caused by a pathogen bearing a guanine riboswitch that controls the expression of guaA, said method comprising contacting a guanine riboswitch with said compound; determining whether said compound binds to said guanine riboswitch; wherein the binding of said compound to said guanine riboswitch is an indication that said compound is suitable for treating said microbial infection.

In a specific embodiment of the method, said guanine riboswitch is the guanine xpt riboswitch from *Streptococcus pyogenes* (STPY-xpt). In another specific embodiment, the method further comprises contacting said guanine riboswitch with guanine or a guanine-like ligand. In another specific embodiment, the method further comprises determining whether said compound may be ribosylated.

In accordance with another aspect of the present invention, there is provided a method for preventing the development of multi-drug resistance of a bacteria in a subject, said method comprising administering a non ribosylable ligand of a guanine riboswitch to the subject, wherein the bacteria bears a guanine riboswitch that controls the expression of guaA.

In accordance with another aspect of the present invention, there is provided a method for preventing the development of multi-drug resistance of a bacteria in a subject, or treating a multidrug resistance of a bacteria in the subject said method comprising administering a non ribosylable ligand of a guanine riboswitch to the subject, wherein the bacteria bears a guanine riboswitch that controls the expression of guaA.

In a specific embodiment of the method, said non ribosylable ligand of a guanine riboswitch is: (i) the compound defined above; (ii) 4-hydroxy-2,5,6-triaminopyrimidine (formula 1.01); (iii) 4,5-diamino-6-hydroxy-2-mercaptopyrimidine (formula 1.16); (iv) 2,4-diamino-6-hydroxypyrimidine (formula 1.13); or (v) 5-amino-2-chloro-2,3-dihydrothiazolo[4,5]pyrimidine-7-(6H)-one (2.17).

In accordance with another aspect of the present invention, there is provided a use of a non ribosylable ligand of a guanine riboswitch for treating a multi-drug resistant bacteria or preventing the development of a multi-drug resistant bacteria, wherein the bacteria bears a guanine riboswitch that controls the expression of guaA.

In accordance with another aspect of the present invention, there is provided a use of a non ribosylable ligand of a guanine riboswitch for the manufacture of a medicament for treating a multi-drug resistant bacteria or preventing the development of a multi-drug resistant bacteria, wherein the bacteria bears a guanine riboswitch that controls the expression of guaA.

In accordance with another aspect of the present invention, there is provided a use of the compound defined above or the above-mentioned composition for treating a multi-drug resistant bacteria or preventing the development of a multi-drug resistant bacteria, wherein the bacteria bears a guanine riboswitch that controls the expression of guaA.

In a specific embodiment of the uses, said non ribosylable ligand of a guanine riboswitch is: (i) the compound defined above; (ii) 4-hydroxy-2,5,6-triaminopyrimidine (formula 1.01); (iii) 4,5-diamino-6-hydroxy-2-mercaptopyrimidine (formula 1.16); (iv) 2,4-diamino-6-hydroxypyrimidine (formula 1.13); or (v) 5-amino-2-chloro-2,3-dihydrothiazolo[4,5]pyrimidine-7-(6H)-one (2.17).

In accordance with another aspect of the present invention there is provided a non ribosylable ligand of a guanine riboswitch (a) for preventing or treating a microbial infection in a subject, wherein said microbial infection is caused by a pathogen bearing the guanine riboswitch, and wherein the guanine riboswitch controls the expression of guaA; or (b) for the disinfection, sterilization and/or antisepsis of an object from a pathogen bearing a guanine riboswitch that controls the expression of guaA; or (c) for treating a multi-drug resistant bacteria or preventing the development of a multi-drug resistant bacteria, wherein the bacteria bears a guanine riboswitch that controls the expression of guaA.

In a specific embodiment of said ligand for the disinfection, sterilization and/or antisepsis of an object, said object is an animal or milk.

In accordance with another aspect of the present invention, there is provided (i) the compound defined above; (ii) 4-hydroxy-2,5,6-triaminopyrimidine (formula 1.01); (iii) 4,5-diamino-6-hydroxy-2-mercaptopyrimidine (formula 1.16); (iv) 2,4-diamino-6-hydroxypyrimidine (formula 1.13); or (v) 5-amino-2-chloro-2,3-dihydrothiazolo[4,5]pyrimidine-7-(6H)-one (2.17), for (a) preventing or treating a microbial infection in a subject, wherein said microbial infection is caused by a pathogen bearing a guanine riboswitch that controls the expression of guaA; or (b) the disinfection, sterilization and/or antisepsis of an object from a pathogen bearing a guanine riboswitch that controls the expression of guaA; or (c) treating a multi-drug resistant bacteria or preventing the development of a multi-drug resistant bacteria, wherein the bacteria bears a guanine riboswitch that controls the expression of guaA.

In a specific embodiment of said composition for the disinfection, sterilization and/or antisepsis of an object, said object is an animal or milk.

In accordance with another aspect of the present invention, there is provided a composition comprising (i) the compound defined in any one of claims 1 to 15; (ii) 4-hydroxy-2,5,6-triaminopyrimidine (formula 1.01); (iii) 4,5-diamino-6-hydroxy-2-mercaptopyrimidine (formula 1.16); (iv) 2,4-diamino-6-hydroxypyrimidine (formula 1.13); or (v) 5-amino-2-chloro-2,3-dihydrothiazolo[4,5]pyrimidine-7-(6H)-one (2.17); and (a) an antibiotic; (b) an antiseptic; (c) a disinfectant; (d) a diluent; (e) an excipient; (f) a pharmaceutically acceptable carrier; or (g) any combination of (a)-(f), said composition being: (aa) for preventing or treating a microbial infection in a subject, wherein said microbial infection is caused by a pathogen bearing the guanine riboswitch, and wherein the guanine riboswitch controls the expression of guaA; or (bb) for the disinfection, sterilization and/or antisepsis of an object from a pathogen bearing a guanine riboswitch that controls the expression of guaA; or (cc) for treating a multi-drug resistant bacteria or preventing the development of a multi-drug resistant bacteria, wherein the bacteria bears a guanine riboswitch that controls the expression of guaA.

In a specific embodiment of the ligands, compounds and compositions for uses described above, said subject is an animal (e.g., cattle such as cow; goat, ewe, ass, horse, pig; cat; dog; etc.). In another specific embodiment, said subject is a cow. In another specific embodiment, said subject is a human. In another specific embodiment, said pathogen is a bacteria belonging to the genus *Staphylococcus* or *Clostridium*. In another specific embodiment, said bacteria is *Staphylococcus aureus*, methicillin-resistant *Staphylococcus aureus, Staphylococcus epidermidis, Staphylococcus haemolyticus, Clostridium botulinum* or *Clostridium difficile*. In another specific embodiment, said infection is a mammary gland infection.

In accordance with another aspect of the present invention, there is provided a kit comprising the compound defined above or the above-mentioned composition, and instructions to use same in the prevention or treatment of a microbial infection.

In a specific embodiment of the kit, the kit comprises: (i) the compound defined above; (ii) 4-hydroxy-2,5,6-triaminopyrimidine (formula 1.01); (iii) 4,5-diamino-6-hydroxy-2-mercaptopyrimidine (formula 1.16); (iv) 2,4-diamino-6-hydroxypyrimidine (formula 1.13); (v) 5-amino-2-chloro-2,3-dihydrothiazolo[4,5]pyrimidine-7-(6H)-one (2.17); or (vi) the composition defined above, and instructions to use same in the prevention or treatment of a microbial infection.

In accordance with another aspect of the present invention, there is provided a method for preparing the compound of formula 2.02

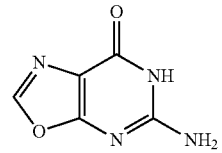

(2.02)

said method comprising (a) reacting diethylacetamido malonate with guanidine hydrochloride in the presence of sodium methoxide and methanol to obtain a solid; (b) dissolving the solid of (a) in an aqueous solution; (c) subjecting the solution of (b) to an acidic precipitation to obtain a 5-formamino-2-amino-4,6-dihydroxypyrimidine precipitate; (d) dissolving the 5-formamino-2-amino-4,6-dihydroxypyrimidine precipitate in an acid; and (e) precipitating the solution of (d) to obtain the compound of formula 2.02.

In a specific embodiment of the method, said reacting is performed under reflux. In another specific embodiment, said acidic precipitation of (b) is performed using a hydrochloric acid (HCl) solution. In another specific embodiment, said HCl solution is a 50% HCl solution. In another specific embodiment, dissolving of (d) is performed using sulfuric acid. In another specific embodiment, said sulfuric acid is 12 M sulfuric acid. In another specific embodiment, the method further comprises washing said solid of (a) with methanol and chloroform. In another specific embodiment, said aqueous solution is water. In another specific embodiment, said precipitating of (e) is performed using tetrahydrofuran (THF).

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 7A shows the growth of *S. aureus* strain ATCC 29213 as a function of ligand concentration in the presence of compound 1.13 (●) or 1.01 (□). FIGS. 7B and 7C show the growth of *S. aureus* strain ATCC 29213 as a function of time in the absence (●) or presence of various compounds including erythromycin (▲), vancomycin (■), ciprofloxacin (◆), and compound 1.01 (▼), at concentrations equivalent to their corresponding minimal inhibitory concentration (MIC) (FIG. 7B) or ¼ of their MIC (FIG. 7C). FIG. 7D shows the growth of *S. aureus* strain ATCC 29213 as a function of time in media alone (●), in the presence of compound 1.01 (▼), or in the presence of compound 1.01 supplemented with GMP (i.e. a molecule normally synthesized by the enzyme GMP synthetase encoded by guaA) (▲).

DESCRIPTION OF ILLUSTRATIVE EMBODIMENTS

Figure 1:
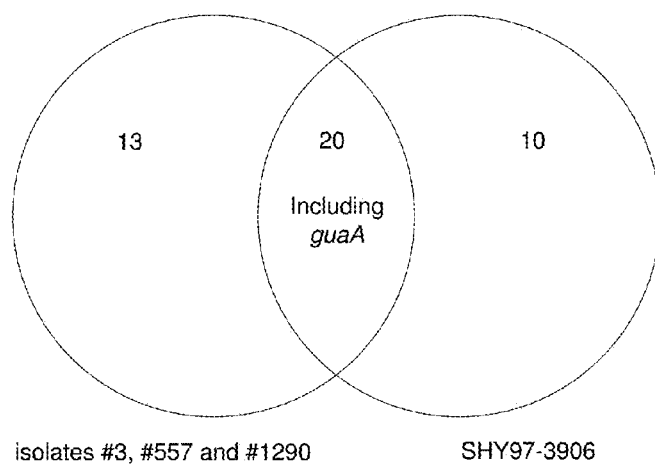
FIG. 1 is a Venn diagram showing the number of genes (including guaA) that are commonly or differentially expressed by a prototypical mastitis *S. aureus* isolate (SHY97-3906) and *S. aureus* isolates causing persistent and chronic bovine mastitis (isolates #3, #557 and #1290).

The gene guaA is essential for the survival or virulence of various microbial pathogens and encodes the enzyme GMP synthetase, which catalyses the synthesis of GMP (guanosine-5'-monophosphate) (E.C. 6.3.5.2) from XMP (xanthosine 5'-monophosphate). The present invention showed that, in some microbial pathogens, expression of the essential gene guaA is under control of the guanine riboswitch. As shown in the accompanying examples, the guanine riboswitch in *S. aureus* was found herein to control the expression of four genes present on the same mRNA transcript: xpt, pbuX, guaB and guaA. A bioinformatic analysis revealed that such guanine riboswitches are found in pathogen microorganisms such as *Staphylococcus aureus* and *Clostridium difficile* but not in microorganisms such as *Bacillus subtilis* and *Streptococci* in which a guanine riboswitch does not control the expression of guaA. See Table 3 below for examples of microorganisms which contain or not a guanine riboswitch that controls the expression of guaA.

The present invention also relates to the unexpected discovery that some pathogen microorganisms, such as *S. aureus*, highly express guaA in specific environments during infection of an animal host such as a mammal. As shown in the accompanying examples, microarray and quantitative PCR gene expression analysis was performed on various *S. aureus* strains isolated from bovine intramammary infections. These studies reveal that guaA is highly expressed during infection in cows by prototypical *S. aureus* strains known to cause bovine mastitis as well as in strains known to cause persistent and chronic mastitis. Therefore, the present invention also relates to the surprising discovery that guanine riboswitches controlling the expression of the guaA gene are suitable targets for therapeutic antimicrobial intervention.

The present invention also relates to the surprising discovery that guanine-like compounds modified to be unable to undergo ribosylation, are nevertheless capable of binding to or interacting with riboswitch aptamers and can affect expression of genes that are under riboswitch control. As shown in the accompanying examples, binding and competition assays measuring the ability of various compounds to displace a known guanine riboswitch ligand showed that the compounds of the present invention are capable of binding to the guanine riboswitch. Microarray gene expression analysis confirmed that the compounds of the present invention can not only bind to guanine riboswitches but also modulate expression of genes under control of the guanine riboswitch. Furthermore, the specificity and mechanism of this modulation was validated by studies combining a compound of the present invention with the metabolite GMP.

The present invention also relates to the discovery that the compounds of the present invention can act as specific or selective antimicrobial agents to which microbial pathogens (that have the guaA gene under control of the guanine riboswitch) cannot develop resistance. The present invention also relates to the discovery that the compounds of the present invention have no substantial inhibitory activity against microorganisms in which the gene guaA is not controlled by a guanine riboswitch. As shown in the accompanying examples, the compounds of the present invention can demonstrate an anti-bacterial effect on *S. aureus* and *C. difficile* strains when grown in vitro (e.g., in culture media or milk) or in vivo (e.g., in mice mammary gland infections). The specificity of the compounds of the present invention was demonstrated by their failure to exert an antibacterial effect on strains (e.g., *E. coli*) lacking a guaA under control of the guanine riboswitch. The anti-bacterial effect of the compounds of the present invention were shown herein to be comparable to several well-known antibiotic compounds. Strikingly, unlike the well-known antibiotic compounds, ciprofloxacin and rifampicin, a *S. aureus* strain did not develop antibiotic resistance to a compound of the present invention. Therefore, it is also disclosed herein that the compounds of the present invention are able to inhibit the expression of the gene guaA, preventing rapid development of bacterial resistance in *S. aureus*.

The present invention also relates to compounds of the following general formulas:

Guanine

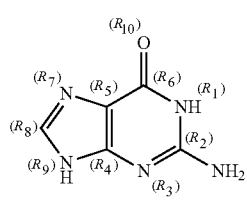

Formula 1.0:

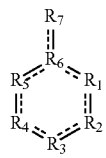

Formula 1.01 (4-hydroxy-2,5,6-triaminopyrimidine here shown as the guanine riboswitch ligand 2,5,6-triaminopyrimidine-4-one):

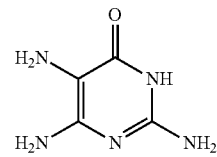

Formula 1.13 (2,4-diamino-6-hydroxypyrimidine here shown as the guanine riboswitch ligand 2,6-diaminopyrimidine-4-one):

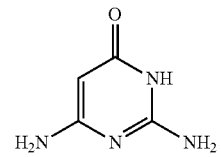

Formula 1.16 (4,5-diamino-6-hydroxy-2-mercaptopyrimidine here shown as the guanine riboswitch ligand 5,6-diamino-2-mercaptopyrimidine-4-one)

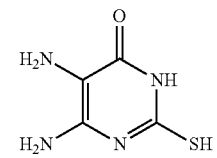

Formula 2.0:

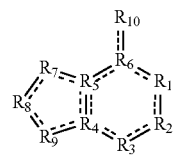

Formula 2.02 (9-oxoguanine here shown as 5-Amino-6H-oxazolo[5,4-d]pyrimidin-7-one)

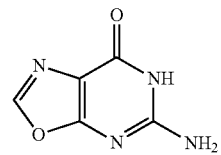

Formula 2.17 (5-amino-2-chloro-2,3-dihydrothiazolo[4,5]pyrimidine-7-(6H)-one)

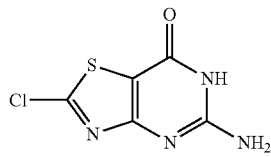 [SMILES: Nc1nc2nc(Cl)sc2c(=O)[nH]1]

Formula 3.0:

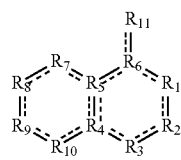

The compounds of the present invention bind to the guanine riboswitch binding site and yet are chemically unable to be ribosylated by the targeted pathogens. This property prevents incorporation of the compounds into cellular nucleosides, nucleotides or nucleic acids, and thus prevents broad, non-specific toxicity for bacterial species not targeted by the compound and for the mammalian or animal host in which the present compounds are used for therapeutic intervention.

Definitions

The use of the word "a" or "an" when used in conjunction with the term "comprising" in the claims and/or the specification may mean "one" but it is also consistent with the meaning of "one or more", "at least one", and "one or more than one".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the terms "molecule", "compound", "agent" or "ligand" are used interchangeably and broadly to refer to natural, synthetic or semi-synthetic molecules or compounds. The term "compound" therefore denotes, for example, chemicals, macromolecules, cell or tissue extracts (from plants or animals) and the like. Non-limiting examples of compounds include peptides, antibodies, carbohydrates, nucleic acid molecules and pharmaceutical agents. The compound can be selected and screened by a variety of means including random screening, rational selection and by rational design using, for example, ligand modeling methods such as computer modeling. The terms "rationally selected" or "rationally designed" are meant to define compounds which have been chosen based on the configuration of interacting domains of the present invention (e.g., the guanine riboswitch). As will be understood by the person of ordinary skill, molecules having non-naturally occurring modifications are also within the scope of the term "compound". For example, the compounds of the present invention can be modified to enhance their activity, stability, toxicity and/or bioavailability. The compounds or molecules identified in accordance with the teachings of the present invention have a therapeutic value in diseases or conditions related to microbial infections.

The term "subject" or "patient" as used herein refers to an animal, preferably a mammal such as but not limited cattle such as cow; goat; ewe; ass; horse; pig; cat; dog; etc. or human who is the object of treatment, observation or experiment.

As used herein, the terms "pharmaceutically acceptable" refer to molecular entities and compositions that are physiologically tolerable and do not typically produce an allergic or similar untoward reaction, such as gastric upset, dizziness and the like, when administered to animals (e.g., cows) or human. Preferably, as used herein, the term "pharmaceutically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin.

Compounds of the invention may be administered in a pharmaceutical composition. Pharmaceutical compositions may be administered in unit dosage form. Any appropriate route of administration may be employed, for example, parenteral, subcutaneous, intramuscular, intramammary, intracranial, intraorbital, ophthalmic, intraventricular, intracapsular, intraarticular, intraspinal, intracisternal, intraperitoneal, intranasal, aerosol, or oral administration. Examples of specific routes of administration include parenteral, e.g., intravenous, intradermal, subcutaneous, intramammary; oral (e.g., inhalation); transdermal (topical); transmucosal, and rectal administration.

Conventional pharmaceutical practice may be employed to provide suitable formulations or compositions to administer such compositions to patients. Methods well known in the art for making pharmaceutical compositions and formulations are found in, for example, Remington: The Science and Practice of Pharmacy, (20th ed.) ed. A. R. Gennaro A R., 2000, Lippincott: Philadelphia.

Therapeutic formulations for oral administration, may be in the form of tablets or capsules; for transmucosal (e.g., rectal, intranasal) or transdermal/percutaneous administration may be in the form of ointments, powders, nasal drops, sprays/aerosols or suppositories; for topical administration, may be in the form of ointments, creams, gels or solutions; for parenteral administration (e.g., intravenously, intramuscularly, intradermal, intramammary, subcutaneously, intrathecally or transdermally), using for example injectable solutions. Furthermore, administration can be carried out sublingually or as ophthalmological preparations or as an aerosol, for example in the form of a spray. Intravenous, intramuscular or oral administration is a preferred form of use.

Oral

For the purpose of oral therapeutic administration, the active compound can be incorporated with excipients and used for example in the form of tablets, troches, dragees, hard or soft gelatin capsules, solutions (e.g., syrups), emulsions or suspensions, or capsules. For the preparation of formulations for oral administration, the compounds of the present invention may be admixed with pharmaceutically inert, inorganic or organic excipients (e.g., pharmaceutically compatible binding agents, and/or adjuvant). The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Examples of suitable excipients for tablets, dragees or hard gelatin capsules for example include lactose, maize starch or derivatives thereof, talc or stearic acid or salts thereof. Suitable excipients for use with soft gelatin capsules include for example vegetable oils, waxes, fats, semi-solid or liquid polyols etc.; according to the nature of the active ingredients it may however be the case that no excipient is needed at all for soft gelatin capsules.

For the preparation of solutions and syrups, excipients which may be used include for example water, polyols, saccharose, invert sugar and glucose.

Nasal

For administration by inhalation, the compounds may be delivered in the form of an aerosol spray from pressured container or dispenser which contains a suitable propellant, e.g., a gas such as carbon dioxide, or a nebulizer. Formulations for inhalation may contain excipients, or example, lactose, or may be aqueous solutions containing, for example, polyoxyethylene-9-lauryl ether, glycocholate and deoxycholate, or may be oily solutions for administration in the form of nasal drops, or as a gel.

Transmucosal or Transdermal

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. For suppositories, and local or percutaneous application, excipients which may be used include for example natural or hardened oils, waxes, fats and semi-solid or liquid polyols.

Parenteral

Pharmaceutical compositions suitable for injectable use include sterile aqueous solutions (where water soluble) or dispersions and sterile powders for the extemporaneous preparation of sterile injectable solutions or dispersion. Solutions or suspensions used for parenteral application can include the following components: a sterile diluent such as water for injection (where water soluble), saline solution, fixed oils (e.g., paraffin oil), polyalkylene glycols such as polyethylene glycols, glycerine, propylene glycol or other synthetic solvents, oils of vegetable origin, or hydrogenated napthalenes; antibacterial agents such as benzyl alcohol or methyl parabens; antioxidants such as ascorbic acid or sodium bisulfite; chelating agents such as ethylenediaminetetraacetic acid; reducing agents such as dithiothreitol, buffers such as acetates, citrates or phosphates and agents for the adjustment of tonicity such as sodium chloride or dextrose. The pH can be adjusted with acids or bases, such as hydrochloric acid or sodium hydroxide. Biocompatible, biodegradable lactide polymer, lactide/glycolide copolymer, or polyoxyethylene-polyoxypropylene copolymers may be used to control the release of the compounds. Other potentially useful parenteral delivery systems for compounds of the invention include ethylenevinyl acetate copolymer particles, osmotic pumps, implantable infusion systems, and liposomes. The parenteral preparation can also be enclosed in ampoules, disposable syringes or multiple dose vials made of glass or plastic.

For intravenous or intramammary administration, suitable carriers include physiological saline, bacteriostatic water, Cremophor EL™ (BASF, Parsippany, N.J.) or phosphate buffered saline (PBS).

Liposomal suspensions (including liposomes targeted to specific cell types) can also be used as pharmaceutically acceptable carriers. A variety of liposomal formulations suitable for delivering a compound to an animal have been described and demonstrated to be effective in delivering a variety of compound, including, e.g., small molecules, nucleic acids, and polypeptides.

As mentioned earlier, medicaments containing the compounds of the present invention are also an object of the present invention, as is a process for the manufacture of such medicaments, which process comprises bringing one or more of the compounds of the present invention to, if desired, one or more other therapeutically valuable substances into a galenical administration form.

Salts, Esters, Hydrates and Solvates

The compounds of the present invention include pharmacologically acceptable salts and ester derivatives thereof as well as hydrates or solvates thereof and all stereoisomeric forms of the referenced compounds. The compounds and pharmacologically acceptable esters thereof of the present invention can form pharmacologically acceptable salts if necessary.

Salts

The terms "pharmacologically acceptable salt thereof" refer to a salt to which the compounds of the present invention can be converted. Preferred examples of such a salt include alkali metal salts such as a sodium salt, a potassium salt, a lithium salt, magnesium or calcium salts; alkaline earth metal salts such as a calcium salt and a magnesium salt; metal salts such as an aluminium salt, an iron salt, a zinc salt, a copper salt, a nickel salt and a cobalt salt; amine salts such as inorganic salts including an ammonium salt; organic salts or ammonium salts such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzyl-phenethylamine salt, a piperazine salt, a tetramethylammonium salt and a tris(hydroxymethyl)aminomethane salt; inorganic acid salts such as hydrohalic acid salts such as a hydrofluoride, a hydrochloride, a hydrobromide or a hydroiodide, a nitrate, a perchlorate, a sulfate or a phosphate; lower alkanesulfonates such as a methanesulfonate, trifluoromethanesulfonate or an ethanesulfonate; arylsulfonates such as a benzenesulfonate or a p-toluenesulfonate and the like, which are non toxic to living organisms; organic acid salts such as an acetate, a malate, adipate, a fumarate, a succinate, a citrate, alginate, ascorbate, benzoate, benzenesulfonate, bisulfate, butyrate, camphorate, camphorsulfonate, cinnamate, cyclopentanepropionate, digluconate, dodecylsulfate, ethanesulfonate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, sulfonate, methanesulfonate, trifluoromethanesulfonates, ethanesulfonates 2-naphthalenesulfonate, nicotinate, nitrate, oxalate, pamoate, pectinate, persulfate, 3-phenylpropionate, picrate, pivalate, propionate, tartrate, thiocyanate, tosylate, and undecanoate, a tartrate, an oxalate or a maleate; and amino acid salts such as a glycine salt, a lysine salt, an arginine salt, an omithine salt, histidine, a glutamate or an aspartate salt. Additionally, basic nitrogen containing groups may be quaternized with such agents as lower alkyl halides such as methyl, ethyl, propyl, and butyl chlorides, bromides and iodides; dialkyl sulfates including dimethyl, diethyl, and dibutyl sulfate; and diamyl sulfates, long chain halides such as decyl, lauryl, myristyl and strearyl chlorides, bromides and iodides, aralkyl halides including benzyl and phenethyl bromides, and others. For further example, see S. M. Berge, et al. "Pharmaceutical Salts," J. Pharm. Sci. 1977, 66, 1-19. Such salts can be formed quite readily by those skilled in the art using standard techniques.

Preferred example of the salts formed with an acidic group present in the compounds of the present invention include metal salts such as alkali metal salts (e.g., sodium salts, potassium salts and lithium salts), alkali earth metal salts (e.g., calcium salts and magnesium salts), aluminum salts and iron salts; amine salts such as inorganic amine salts (e.g., ammonium salts) and organic amine salts (e.g., t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts. N-benzylphenethylamine salts, piperazine salts, tetramethylammonium salts and tris(hydroxymethyl)aminomethane salts; and amino acid salts such as glycine salts, lysine salts, arginine salts, ornithine salts, glutamates and aspartates.

All salts are intended to be pharmaceutically acceptable salts within the scope of the invention and all salts are considered equivalent to the free forms of the corresponding compounds for purposes of the invention.

Esters

Physiologically/pharmaceutically acceptable esters are also useful as active medicaments. The term "pharmaceutically acceptable esters" embraces esters of the compounds of the present invention, in which hydroxy groups (e.g., in carboxylic acid) have been converted to the corresponding esters and may act as a prodrug which, when absorbed into the bloodstream of a warm-blooded animal, may cleave in such a manner as to release the drug form and permit the drug to afford improved therapeutic efficacy. Such esters can be formed with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms. Further examples are the esters with aliphatic or aromatic acids such as acetic acid or with aliphatic alcohol (e.g., alkyl esters, including methyl, ethyl, propyl, isopropyl, butyl, isobutyl or pentyl esters, and the like) or aromatic alcohols (e.g., benzyl ester)

Esters can be prepared from their corresponding acids or salts by a variety of methods known to those skilled in the art, such as, for example, by first transforming the acid to the acid chloride and then reacting the acid chloride with a suitable alcohol. Other suitable methods for making esters are described in Kemp and Vellaccio, 1980.

Where esters of the invention have a basic group, such as an amino group, the compound can be converted to a salt by reacting it with an acid, and in the case where the esters have an acidic group, such as a sulfonamide group, the compound can be converted to a salt by reacting it with a base. The compounds of the present invention encompass such salts.

Salts and esters of the compounds of the present invention may be prepared by known method by employing appropriate starting materials or intermediate compounds that are readily available and/or are described herein.

Generally, a desired salt of a compound of this invention can be prepared in situ during the final isolation and purification of a compound by means well known in the art. For example, a desired salt can be prepared by separately reacting the purified compound in its free base or free acid form with a suitable organic or inorganic acid, or suitable organic or inorganic base, respectively, and isolating the salt thus formed. In the case of basic compounds, for example, the free base is treated with anhydrous HCl in a suitable solvent such as THF, and the salt isolated as a hydrochloride salt. In the case of acidic compounds, the salts may be obtained, for example, by treatment of the free acid with anhydrous ammonia in a suitable solvent such as ether and subsequent isolation of the ammonium salt. These methods are conventional and would be readily apparent to one skilled in the art.

The compounds of this invention may be esterified by a variety of conventional procedures including reacting the appropriate anhydride, carboxylic acid or acid chloride with the alcohol group of a compound of this invention. The appropriate anhydride is reacted with the alcohol in the presence of a base to facilitate acylation such as 1,8-bis[dimethylamino]naphthalene or N,N-dimethylaminopyridine. Or, an appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be effected using the appropriate carboxylic acid in the presence of trifluoroacetic anhydride and, optionally, pyridine, or in the presence of N,N-carbonyldiimidazole with pyridine. Reaction of an acid chloride with the alcohol can be carried out with an acylation catalyst such as 4-DMAP or pyridine.

One skilled in the art would readily know how to successfully carry out these as well as other known methods of esterification of alcohols.

Hydrates

As used herein the terms, "pharmaceutically acceptable hydrate" refer to the compounds of the instant invention crystallized with one or more molecules of water to form a hydrated form.

Prodrugs and Solvates

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of the present invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention or a pharmaceutically acceptable salt, hydrate or solvate of the compound contains a carboxylic acid functional group, a prodrug can comprise an ester formed by the replacement of the hydrogen atom of the acid group with a group such as, for example, (C1-C8)alkyl, (C2-C12)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C1-C2)alkylamino(C2-C3)alkyl (such as β-dimethylamino-ethyl), carbamoyl-(C1-C2)alkyl, N,N-di(C1-C2)alkylcarbamoyl-(C1-C2)alkyl and piperidino-, pyrrolidino- or morpholino(C2-C3)alkyl, and the like.

Similarly, if a compound of the present invention contains an alcohol functional group, a prodrug can be formed by the replacement of the hydrogen atom of the alcohol group with a group such as, for example, (C1-C6)alkanoyloxymethyl, 1-((C1-C6)alkanoyloxy)ethyl, 1-methyl-1-((C1-C6)alkanoyloxy)ethyl, (C1-C6)alkoxycarbonyloxymethyl, N—(C1-C6)alkoxycarbonylaminomethyl, succinoyl, (C1-C6)alkanoyl, α-amino(C1-C4)alkanyl, arylacyl and α-aminoacyl, or α-aminoacyl-α-aminoacyl, where each α-aminoacyl group is independently selected from the naturally occurring L-amino acids, P(O)(OH)2, —P(O)(O(C1-C6)alkyl)2 or glycosyl (the radical resulting from the removal of a hydroxyl group of the hemiacetal form of a carbohydrate), and the like.

If a compound of the present invention incorporates an amine functional group, a prodrug can be formed by the replacement of a hydrogen atom in the amine group with a group such as, for example, R-carbonyl, RO-carbonyl, NRR'-carbonyl where R and R' are each independently (C1-C10)alkyl, (C3-C7)cycloalkyl, benzyl, or R-carbonyl is a natural α-aminoacyl or natural α-aminoacyl, —C(OH)C(O)OY1 wherein Y1 is H, (C1-C6)alkyl or benzyl, —C(OY2)Y3 wherein Y2 is (C1-C4) alkyl and Y3 is (C1-C6)alkyl, carboxy (C1-C6)alkyl, amino(C1-C4)alkyl or mono-N— or di-N,N—(C1-C6)alkylaminoalkyl, —C(Y4)Y5 wherein Y4 is H or methyl and Y5 is mono-N— or di-N,N—(C1-C6)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS Pharm Sci Tech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Stereoisomers, Enantiomers, Racemates, Tautomers

The compounds of the present invention have asymmetric carbon atoms and can exist in the form of optically pure enantiomers or as racemates. The invention embraces all of these forms.

For purposes of this Specification, "pharmaceutically acceptable tautomer" means any tautomeric form of any compound of the present invention.

The purification of enantiomers and the separation of isomeric mixtures of a compound of the present invention may be accomplished by standard techniques known in the art.

The pharmaceutical compositions may also contain preserving agents, solubilising agents, stabilising agents, wetting agents, emulsifiers, sweeteners, colorants, odorants, salts for the variation of osmotic pressure, buffers, coating agents or antioxidants. As mentioned earlier, they may also contain other therapeutically valuable agents.

Dosages

The dosages in which the compounds of the present invention are administered in effective amounts depend on the nature of the specific active ingredient, the age and the requirements of the patient and the mode of application. In general, daily dosages of about 1 mg-1000 mg, preferably 5 mg-500 mg, per day come into consideration.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the present invention can include a series of treatments.

Toxicity and Therapeutic Efficacy

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Kits

The present invention also encompasses kits comprising the compounds of the present invention. For example, the kit can comprise one or more compounds or agents binding to a guanine riboswitch and inhibit or reduce the expression of the gene guaA. The kit may optionally include one or more control samples. The compounds or agents can be packaged in a suitable container. The kit can further comprise instructions for using the kit.

The present invention also relates to methods for preparing the above-mentioned compounds. In an embodiment, the above-mentioned method is that defined in Examples 13 and 16 below.

The present invention is illustrated in further details by the following non-limiting examples.

Example 1 guaA Expression in S. Aureus Isolates from Infected Cows and from Milk

The present invention relates to the discovery that some pathogen microorganisms, such as S. aureus, sustain a significant level of expression of the gene guaA (comparable to some known essential genes) in specific environments during infection of a mammalian or animal host. The present invention also discloses the sustained expression of guaA in several S. aureus isolates, including those causing persistent and chronic bovine mastitis, during infection in a cow. The present invention also discloses that the expression of guaA in several S. aureus isolates, including those causing persistent and chronic bovine mastitis, was relatively higher during infection in cows compared to the expression of guaA in the corresponding S. aureus isolates grown in vitro in freshly collected milk obtained from a healthy cow.

DNA microarray gene expression analysis was used to identify genes that were expressed (at different time points) by various S. aureus strains in vivo during bovine mastitis. Mastitis infection in two cows were examined: Cow #310 and cow #5325. The results of this analysis with respect to all genes are summarized in the Venn diagram presented in FIG. 1. Briefly, the chip was produced from genes amplified and selected in inventor's laboratory. FIG. 1 shows the number of genes (including guaA) that are commonly or differentially expressed by a prototypical S. aureus mastitis isolate (SHY97-3906) and S. aureus isolates causing persistent and chronic bovine mastitis (isolates #3, #557 and #1290). The results of this microarray analysis with respect to expression of guaA, are summarized in Table 1 below. Although guaA mRNA expression was detected in all samples analyzed, most of the samples showed that guaA was expressed at a level higher than the average level of expression for all genes detected on the arrays (Table 1). These results appear to indicate that, even though the different S. aureus strains (prototypical and chronic) show some differences in the genes they each express, guaA is commonly expressed by both the prototypical mastitis strain (SHY97-3906) and the group of chronic strains (#3, #557 and #1290). Also, the level of expression of guaA, measured by real-time PCR for strain #1290 isolated from three different samples of mastitic milk in vivo, was very similar to that measured for gyrB (1.19±0.33 fold vs. gyrB), demonstrating that guaA is expressed during infection at levels comparable to the well-known S. aureus essential gene gyrB, which encodes an essential DNA gyrase (Anderson et al., 2000).

TABLE 1

Mastitic milk samples in which the expression of guaA was shown to be greater than the average expression of all genes on microarrays for 4 different S. aureus strains at 2 different time points in two animals.

| | | S. aureus strains | | | |
| --- | --- | --- | --- | --- | --- |
| Cow | Day of infection | SHY97-3609 | 3 | 557 | 1290 |
| 310 | 8 | ● | ● | ● | ● |
| 310 | 10 | ● | ● | ● | ● |
| 5325 | 10 | ○ | ● | ⊘ | ⊘ |

Symbols:
●, expression of guaA greater than the average expression of all genes on arrays;
○, expression of guaA was detected but was below the average expression of all genes on arrays;
⊘, not tested by DNA arrays.

Figure 2:
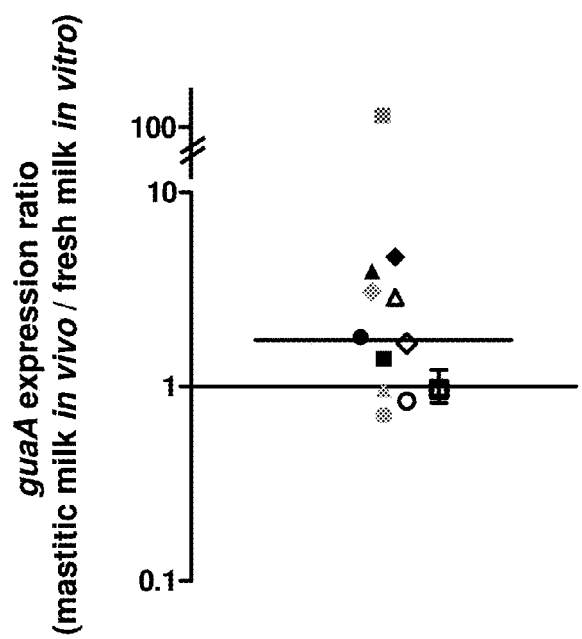
FIG. 2 displays a quantitative PCR analysis showing the relative level of guaA mRNA expression by mastitis isolates of *S. aureus* in the in vivo cow-collected samples compared to when the corresponding *S. aureus* isolates were grown in vitro in freshly collected milk from a healthy cow. All results were normalized to the level of expression of the *S. aureus* gene gyrB. The horizontal bar represents the median. RNA samples from *S. aureus* grown in two different animals were analyzed: cow #5325 at day 10 of infection with strain SHY97-3906 (○), #3 (Δ), #557 (◇), #1290 (□). The same shapes were used for the four different strains for the samples coming from cow #307 at day 8 of infection (black) and cow #307 at day 14 (grey). Quantitative PCR was also done in triplicate for the RNA sample recovered from strain #1290 in cow 5325 at day 10 of infection and the error bar is shown accordingly.

Depicted in FIG. 2 are quantitative PCR analyses showing the relative level of guaA mRNA expression by mastitis isolates of S. aureus in the in vivo cow-collected samples compared to when the corresponding S. aureus isolates were grown in vitro in freshly collected milk from a healthy cow. All results were normalized using the level of expression of S. aureus essential gene, gyrB. The horizontal bar represents the median. RNA samples from S. aureus grown in two different animals were analyzed: cow #5325 at day 10 of infection with strain SHY97-3906 (○), #3 (Δ), #557 (◇), #1290 (□). The same shapes were used for the four different strains for the samples coming from cow #307 at day 8 of infection (black) and cow #307 at day 14 (grey). Quantitative PCR was also done in triplicate for the RNA sample recovered from strain #1290 in cow 5325 at day 10 of infection and the error bar is shown accordingly.

Briefly, four different Staphylococcus aureus strains (clinical isolate SHY97-3906 and chronic isolates 3, 557 and 1290) were inoculated in 8 multiparous Holstein cows in mid lactation at the Dairy and Swine Research and Development Centre of Agriculture and Agri-Food Canada in Sherbrooke, QC, Canada. Each quarter of the mammary gland of the cows was infused with 50 CFU of each S. aureus strain. After the inoculation, milk was collected from each quarter of each cow every 2-4 days in the morning for a total of 18 days. S. aureus was then isolated from the mastitic milk and RNA was extracted from the in vivo grown S. aureus. With the RNA, fluorescent probes for hybridization to DNA arrays were generated through an aminoallyl cDNA labelling procedure. The fluorescent probes (labeled with Cy5) were hybridized to a DNA array that contained a selection of 530 known or putative genes. Only genes with a Cy5 signal intensity of 100%, i.e., greater or equal to the mean Cy5 intensity of the entire array were analyzed. The results were confirmed by quantitative PCR and the level of expression of genes found to be strongly expressed during mastitis by S. aureus was compared to that of in vitro grown S. aureus. FIG. 2 shows that guaA is expressed at level that is roughly equivalent to or higher than the essential gene gyrB in S. aureus present in mastitic milk (Mayer et al, 1988).

Example 2

Polycistronic RNA Encoding xpt/pbuX/guaB/guaA

The present invention relates to the discovery that the guanine riboswitch of S. aureus controls the expression of a polycistronic mRNA encoding xpt/pbuX/guaB/guaA and not only the non-essential genes xpt and pbuX, contradicting the teachings of the prior art that the S. aureus guanine riboswitch controls genes that are not essential for survival or virulence of the pathogen. Example 1 showed that there was a sustained expression of guaA in S. aureus during infection in cows.

Figure 3A:
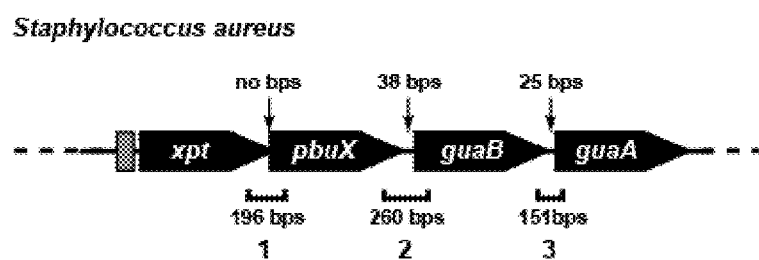
FIG. 3A shows a schematic representation of the structure of the operon xpt/pbuX/guaB/guaA from *S. aureus* as redefined herein with the number of base pairs (bps) present in the intergenic regions (numbers on top) and shows the fragment length in base pairs for the regions amplified by RT-PCR in FIG. 3B (numbers underneath the bars 1, 2 and 3).
Figure 3B:
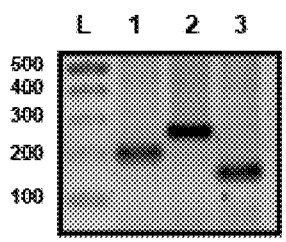
FIG. 3B shows the results of an RT-PCR analysis of the intergenic regions between xpt and pbuX (1); pbuX and guaB (2); and guaB and guaA (3).

Shown in FIG. 3A is a schematic representation of the structure of the operon xpt/pbuX/guaB/guaA from S. aureus as redefined herein with the number of base pairs present in the intergenic regions indicated. A gray rectangle represents the guanine riboswitch. Annotated arrows indicate the number of bases between adjacent genes. This schematic representation was compiled from the results of an RT-PCR analysis of total RNA from S. aureus (FIG. 3B) of the intergenic regions between xpt and pbuX (1); pbuX and guaB (2); and guaB and guaA (3). Briefly, total RNA extract from S. aureus was submitted to DNAse1 followed by reverse transcription. The obtained cDNA was then amplified by PCR using the following primer designed to amplify intergenic region. These results clearly demonstrate the polycistronic nature of the mRNA transcript downstream of the guanine riboswitch.

Example 3

Ability of Compounds of the Invention to Bind Guanine Riboswitches

The compounds of the present invention are able to compete with guanine-like ligands for binding to the guanine riboswitch. Structural modifications of these and other related compounds influence this property.

Figure 4A:
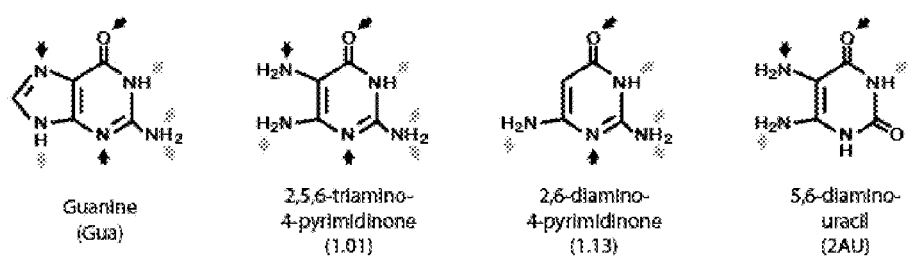
FIG. 4A shows the structure of some guanine riboswitch ligands such as the compounds: 4-hydroxy-2,5,6-triaminopyrimidine shown as 2,5,6-triaminopyrimidine-4-one (compound 1.01), 2,4-diamino-6-hydroxypyrimidine shown as 2,6-diaminopyrimidine-4-one (compound 1.13) and 5,6-diamino-uracil (2AU) as well as their predicted hydrogen bonds. Black and grey arrows stand for hydrogen acceptor and donor groups, respectively.
Figure 4B:
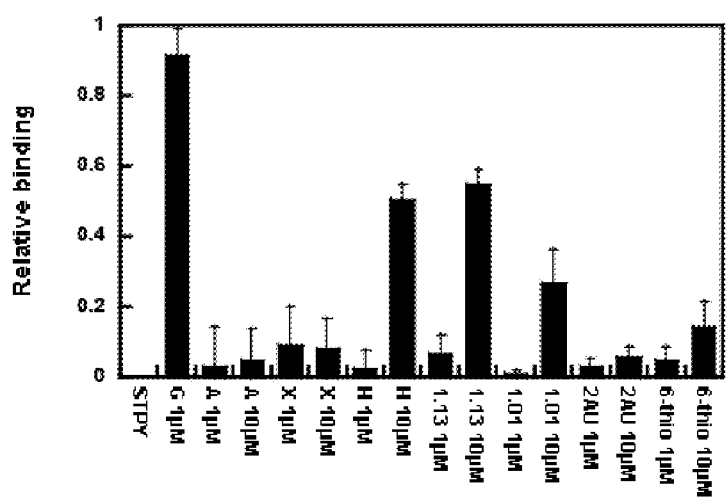
FIG. 4B shows a histogram representing the relative binding affinity of several compounds at two concentrations (1 or 10 µM) for a guanine xpt riboswitch from *Streptococcus pyogenes* (STPY-xpt) as measured using the assay described in Mulhbacher and Lafontaine, 2007. Compounds tested include: guanine (G or Gua), adenine (A), xanthine (X), hypoxanthine (H), compound 1.13, compound 1.01, 5,6-diamino-uracil (2AU) and 6-thioguanine (6-thio).

Shown in FIG. 4A is the structure of the guanine ligand and the compounds: 4-hydroxy-2,5,6-triaminopyrimidine shown as 2,5,6-triaminopyrimidine-4-one (compound 1.01), 2,4-diamino-6-hydroxypyrimidine shown as 2,6-diaminopyrimidine-4-one (compound 1.13) and 5,6-diamino-uracil (2AU) as well as their predicted hydrogen bonds (arrows). FIG. 4B shows a histogram representing the relative binding affinity of several compounds (i.e. guanine (G or Gua), adenine (A), xanthine (X), hypoxanthine (H), compound 1.13, compound 1.01, 5,6-diamino-uracil (2AU) and 6-thioguanine (6-thio)) at two concentrations (1 or 10 µM) for a guanine xpt riboswitch from Streptococcus pyogenes (STPY-xpt). The experiment was performed as in for example Mulhbacher and Lafontaine, 2007. Compounds 1.01 and 1.13 were purchased from Fluka product numbers 17376 and 33050 respectively. Briefly, STPY-xpt aptamers were incubated in the presence of the guanine-like ligand 2-aminopurine alone (Neg. control) or in the presence of 1 or 10 µM of the above-listed compounds. The relative binding affinity was obtained from the ability of a ligand to displace the 2-aminopurine from the guanine riboswitch STPY-xpt aptamer. The results comparing the relative binding of 1 µM guanine with 10 µM of the various tested compounds are summarized in Table 2 below. The phrase "appropriate properties" is meant to refer to structural characteristics enabling compounds to fit or interact with the active site of the guanine riboswitch, while lacking the chemistry required to undergo ribosylation, thus precluding the compounds incorporation into cellular nucleosides, nucleotides or nucleic acids of non targeted bacteria or of the mammalian host treated with the compounds.

TABLE 2

Description of the properties of various known guanine riboswitch ligands

| Compound | Structure | Relative binding | Ribosylation | Appropriate properties |
|---|---|---|---|---|
| guanine (1 µM) | | 1 | Yes | No |
| hypoxanthine (10 µM) | | 0.50 | Yes | No |
| xanthine (10 µM) | | 0.08 | Yes | No |

TABLE 2-continued

Description of the properties of various known guanine riboswitch ligands

| Compound | Structure | Relative binding | Ribosylation | Appropriate properties |
|---|---|---|---|---|
| adenine (10 µM) | | 0.05 | Yes | No |
| 6-thioguanine (10 µM) | | 0.14 | Yes | No |
| 5,6-diamino-uridine (10 µM) | | 0.05 | Yes | No |
| Compound 1.01 (10 µM) | | 0.26 | No | Yes |
| Compound 1.13 (10 µM) | | 0.39 | No | Yes |

Example 4

Growth Inhibition of Bacterial Species Possessing a Guanine Riboswitch that Controls the Expression of the guaA Gene by Compounds of the Present Invention As disclosed herein, compounds of the present invention (such as 4-hydroxy-2,5,6-triaminopyrimidine (compound 1.01)) are able to inhibit the growth of bacteria if such bacteria possess a guanine riboswitch that controls the expression of the guaA gene. Also, the compounds of the present invention (e.g., compound 1.01) do not substantially inhibit the growth of bacteria that have the guaA gene but not the guanine riboswitch that controls its expression.

Shown in Table 3 below are examples of the genes and operons controlled by guanine riboswitches in several bacterial species following a bioinformatic analysis involving a sequence homology algorithm as described in Mulhbacher and Lafontaine, 2007. Briefly, the identification of riboswitches controlling guaA was realized using the Rfam database or a published article (Barrick J E and Breaker R R, Genome Biol. 2007) which repertories guanine riboswitches. The NCBI database was then blasted to find the associate genes. The identification of new guanine riboswitches in newly sequenced genomes could also be realized using the RNAmotif™ solftware. Genes corresponding to guaA are highlighted. Accession numbers for the genome of the bacterium and positions corresponding to the beginning of the riboswitch and of the gene or the operon containing guaA are also presented. Consistent with the teachings of the present invention, bacterial strains (e.g., *S. aureus* and *C. difficile*) expressing the guaA gene under the control of a guanine riboswitch are expected to be susceptible to the antimicrobial effects of the compounds of the present invention. Also consistent with the teachings of the present invention, bacterial strains expressing the guaA gene independently from the guanine riboswitch (e.g., *E. coli* and *Bacillus subtilis*) are expected to be not significantly affected by the antimicrobial effects of the compounds of the present invention.

TABLE 3

Genes and operons controlled by guanine riboswitches in various bacterial strains

| Bacteria | Gram | gene or operon controlled by guanine riboswitch | guaA or operon containing guaA controlled by guanine riboswitch | genome | guanine riboswitch starting | guaA or operon containing guaA ending |
|---|---|---|---|---|---|---|
| Acholeplasma_laidlawii | + | uraA | | | | |
| Alkaliphilus_metalliredigens | + | xpt; purE | guaA | NC_009633 | 944301 | 947544 |
| Alkaliphilus_oremlandii | + | pur operon | guaA | NC_009922 | 582562 | 585305 |
| Bacillus_amyloliquefaciens | + | xpt, pbuX operon; pbuG; pur operon | | | | |
| Bacillus_anthracis | + | uraA; GntR; xpt, pbuX operon; pur operon; nupC | guaA | NC_003997<br>NC_007530<br>NC_005945 | 260657<br>260657<br>260670 | 262446<br>262446<br>262459 |
| Bacillus_cereus | + | pbuG; pur operon; xpt, pbuX operon; GntR; nupC | guaA | NC_012472<br>NC_011658<br>NC_011773<br>NC_004722<br>NC_003909<br>NC_011725<br>NC_011772<br>NC_011969<br>NC_006274<br>NC_009674 | 272003<br>269262<br>261264<br>259617<br>294525<br>259207<br>251188<br>266283<br>265891<br>271090 | 273792<br>271050<br>263053<br>261405<br>296313<br>260995<br>252976<br>268071<br>267680<br>272876 |
| Bacillus_clausii | + | pbuG; pur operon; xpt, pbuX operon | | | | |
| Bacillus_halodurans | + | xpt, pbuX operon; pur Operon; uraA | guaA | NC_002570 | 648458 | 650224 |
| Bacillus_licheniformis | + | pur operon; xpt, pbuX operon; pbuG; nupG | | | | |
| Bacillus_pumilus | + | pbuG; xpt, pbuX operon; uraA; pur operon | | | | |
| Bacillus_subtilis | + | pbuG; pur operon; yxjA; xpt, pbuX operon | | | | |
| Bacillus_thuringiensis | + | pbuG; pur operon; xpt, pbuX operon; GntR; nupC | guaA | NC_008600<br>NC_005957 | 274659<br>266593 | 276448<br>268382 |
| Bacillus_weihenstephanensis | + | uraA; pur operon; xpt, pbuX operon; GntR; nupC | guaA | NC_010184 | 262234 | 264023 |
| Bdellovibrio_bacteriovorus | − | putative secreted nuclease; hypothetical protein | | | | |
| Clostridium_acetobutylicum | + | uraA; xptpbuX operon | guaB, guaA operon | NC_003030 | 2824936 | 2821591 |
| Clostridium_beijerinckii | + | uraA; xptpbuX operon | guaB, guaA operon | NC_009617 | 398946 | 402351 |
| Clostridium_botulinum | + | uraA; pur operon; pbuX, xpt operon; uraA, apt operon; uraA | guaB, guaA operon | NC_009495<br>NC_010520<br>NC_009697<br>NC_009698<br>NC_010516<br>NC_010674<br>NC_010723<br>NC_009699 | 3506948<br>3584820<br>3482936<br>3380044<br>3567858<br>396433<br>391849<br>3600582 | 3503782<br>3581653<br>3479770<br>3376878<br>3564691<br>399735<br>395150<br>3597415 |
| Clostridium_difficile | + | uraA; xpt; pbuX | guaA | NC_009089 | 256232 | 258074 |
| Clostridium_kluyveri | + | uraA | | | | |
| Clostridium_novyi | + | xpt, pbuG | guaB, guaA operon | NC_008593 | 2143257 | 2139825 |
| Clostridium_perfringens | + | xpt; uraA | guaB, guaA operon | NC_003366<br>NC_008261<br>NC_008262 | 2618404<br>2822240<br>2482608 | 2615047<br>2818882<br>2479246 |
| Clostridium_tetani | + | | guaB, guaA operon | NC_004557 | 2551375 | 2549717 |
| Desulfitobacterium_hafniense | + | purL | | | | |
| Desulfotomaculum_reducens | + | add; uraA, purE operon; uraA; adenylosuccinate lyase | | | | |
| Enterococcus_faecalis | + | xpt, pbuX, pur operon | | | | |
| Exiguobacterium_sibiricum | + | xpt, pbuX operon; uraA; pur operon | guaA | NC_010556 | 459675 | 461411 |
| Fusobacterium_nucleatum | − | pur operon | | | | |
| Geobacillus_kaustophilus | + | pbuG; pur operon | guaA | NC_006510 | 272489 | 274168 |
| Geobacillus_thermodenitrificans | + | pbuG; pur operon; xpt, pbuX operon | guaA | NC_009328 | 252216 | 253897 |
| Lactobacillus_acidophilus | + | uraA, pbuG operon; xpt, pbuX operon | | | | |
| Lactobacillus_brevis | + | uraA | | | | |
| Lactobacillus_delbrueckii_bulgaricus | + | xpt, pbuX operon | | | | |

TABLE 3-continued

Genes and operons controlled by guanine riboswitches in various bacterial strains

| Bacteria | Gram | gene or operon controlled by guanine riboswitch | guaA or operon containing guaA controlled by guanine riboswitch | genome | guanine riboswitch starting | guaA or operon containing guaA ending |
|---|---|---|---|---|---|---|
| Lactobacillus_fermentum | + | uraA | | | | |
| Lactobacillus_gasseri | + | uraA | | | | |
| Lactobacillus_helveticus | + | uraA | | | | |
| Lactobacillus_johnsonii | + | uraA | | | | |
| Lactobacillus_plantarum | + | uraA; add | | | | |
| Lactobacillus_reuteri | + | uraA | | | | |
| Lactobacillus_salivarius | + | xpt, pbuX | | | | |
| Lactococcus_lactis | + | xpt, pbuX | | | | |
| Leuconostoc_mesenteroides | + | uraA | | | | |
| Listeria_innocua | + | xpt, pbuX operon; uraA | | | | |
| Listeria_monocytogenes | + | xpt, pbuX operon; uraA | | | | |
| Listeria_welshimeri | + | xpt, pbuX operon; uraA | | | | |
| Lysinibacillus_sphaericus | + | uraA, pbuG operon; pur operon; xpt, pbuX operon; pbuE | guaA | NC_010382 | 217326 | 219120 |
| Oceanobacillus_iheyensis | + | xpt, pbuX operon | guaA | NC_004193 | 760489 | 762329 |
| Oenococcus_oeni | + | guaB; xpt, pbuX operon | | | | |
| Pediococcus_pentosaceus | + | uraA | | | | |
| Shewanella_halifaxensis | − | uraA | | | | |
| Shewanella_pealeana | − | uraA | | | | |
| Staphylococcus_aureus | + | | xpt, pbuX, guaB, guaA operon | NC_002951 | 460076 | 465308 |
| | | | | NC_009632 | 466145 | 471377 |
| | | | | NC_009487 | 466075 | 471307 |
| | | | | NC_003923 | 410563 | 415795 |
| | | | | NC_009782 | 430774 | 436006 |
| | | | | NC_002758 | 430771 | 436003 |
| | | | | NC_002745 | 430814 | 436046 |
| | | | | NC_007795 | 378013 | 383245 |
| | | | | NC_009641 | 425751 | 430983 |
| | | | | NC_007622 | 383514 | 388746 |
| | | | | NC_007793 | 436156 | 441388 |
| | | | | NC_010079 | 436051 | 441283 |
| | | | | NC_002952 | 441067 | 446299 |
| | | | | NC_002953 | 409208 | 414440 |
| Staphylococcus_carnosus | + | | xpt, pbuX, guaB, guaA operon | NC_012121 | 46344 | 51725 |
| Staphylococcus_epidermidis | + | | xpt, pbuX, guaB, guaA operon | NC_004461 | 2433030 | 2427604 |
| | | | | NC_002976 | 54833 | 60259 |
| Staphylococcus_haemoliticus | + | | xpt, pbuX, guaB, guaA operon | NC_007168 | 2598923 | 2593514 |
| Staphylococcus_saprophyticus | + | | xpt, pbuX, guaB, guaA operon | NC_007350 | 2407693 | 2403978 |
| Streptococcus_agalactiae | + | xpt, pbuX operon | | | | |
| Streptococcus_pneumoniae | + | xpt, pbuX operon | | | | |
| Streptococcus_pyogenes | + | xpt, pbuX operon | | | | |
| Streptococcus_thermophilus | + | xpt, pbuX operon | | | | |
| Thermoanaerobacter_pseudethanolicus | + | uraA | guaA | NC_010321 | 1760593 | 1758904 |
| Thermoanaerobacter_X514 | + | uraA | guaA | NC_010320 | 528317 | 531544 |
| Thermoanaerobacter_tengcongensis | + | uraA/purE | | | | |
| Vibrio_sp | − | uraA | | | | |
| Vibrio_splendidus | − | uraA | | | | |

Figure 5A:
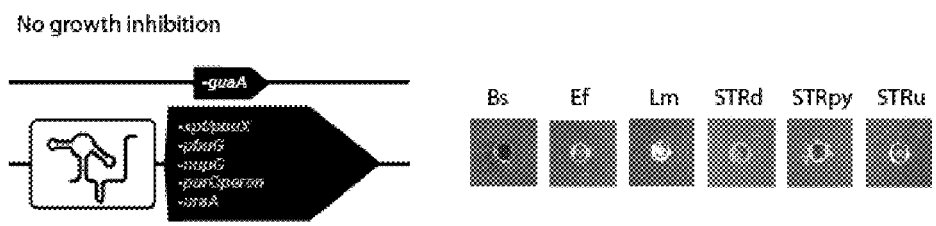
FIGS. 5A and 5B show the effect of compound 1.01 on the growth of various bacterial species in which the guanine riboswitch controls (FIG. 5B) or not (FIG. 5A) the expression of the guaA gene. While strains insensitive to compound 1.01 do not have the expression of guaA under control of a riboswitch (Bs: *Bacillus subtilis*, Ef: *Enterococcus feacium*, Lm: *Listeria monocytogenes*, STRd: *Streptococcus dysgalactiae*, STRpy: *Streptococus pyogenes*, and STRu: *Streptococcus uberis*), the strains susceptible to compound 1.01 control guaA expression via a riboswitch mechanism (Bh: *Bacillus halodurans*, STAh: *S. haemolyticus*, STAa: *S. aureus* ATCC29213, SA228a: *S. aureus* resistant to beta-lactams, erythromycin, ciprofloxacin, gentamicin and tetracycline, MRSAcol: methicilin resistant *S. aureus* COL, Cb: *Clostridium botulinum*; Cd6: virulent *Clostridium difficile* isolated in Quebec; Cd630: *Clostridium difficile* strain 630 with complete sequenced genome; STAe: *S. epidermidis*).
Figure 5B:
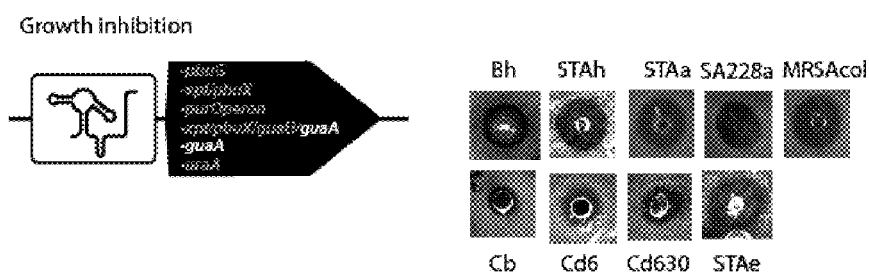

FIG. 5 depicts antibiograms showing the effect of compound 1.01 on the growth of various bacterial species in which the guanine riboswitch controls (FIG. 5B) (i.e. Bh: *Bacillus halodurans*; STAh: *S. haemolyticus*; STAa: *S. aureus* ATCC29213; SA228a: *S. aureus* resistant to beta-lactams, erythromycin, ciprofloxacin, gentamicin and tetracycline; MRSAcol: methicilin resistant *S. aureus* col; Cb: *Clostridium botulinum*; Cd6: *Clostridium difficile* virulent isolated in Quebec; Cd630: *Clostridium difficile* strain 630 with complete sequenced genome; and STAe: *S. epidermidis*) or not (FIG. 5A) (i.e. Bs: *Bacillus subtilis*; Ef: *Enterococcus feacium*; Lm: *Listeria monocytogenes*; STRd: *Streptococcus dysgalactiae*; STRpy: *Streptococus pyogenes*; and STRu: *Streptococcus uberis*) the expression of the essential guaA gene. Briefly, for each strain, bacteria were inoculated at $10^5$ CFU/mL by dilution in Muller-Hinton agar. After agar medium was solidified six wells of 4 mm diameter were made and filled with 15 μl of tested molecule (5 mg/mL). While strains insensitive to compound 1.01 (shown in FIG. 5A) do not have the expression of guaA under control of a riboswitch, the strains sensitive to compound 1.01 (shown in FIG. 5B) control guaA expression via a riboswitch mechanism.

Example 5

Preclusion from Ribosylation of the Compounds of the Present Invention

Figure 6A:
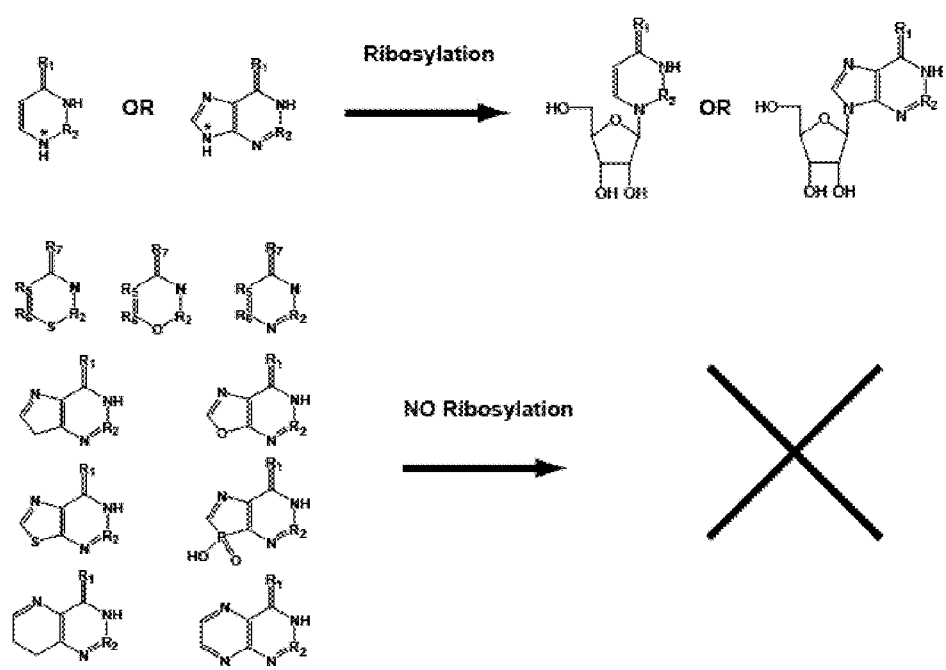
FIG. 6A shows the ribosylation reaction leading to the formation of nucleosides as well as examples of compounds of the invention that would prevent this ribosylation to occur. Asterisks (*) denote the position where chemical modification precludes ribosylation.
Figure 6B:
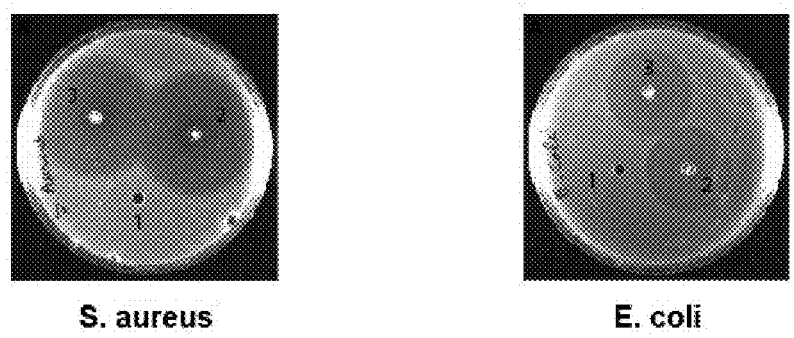
FIG. 6B shows typical antibiograms performed on strains of *E. coli* ATCC 35695 (lacking a guaA riboswitch) and Methicilin Resistant *S. aureus* (containing a guaA riboswitch) grown in the absence (1) or presence of 6-thioguanine at a concentration of 0.5 mg/mL (2) or 1 mg/mL (3).
Figure 6C:
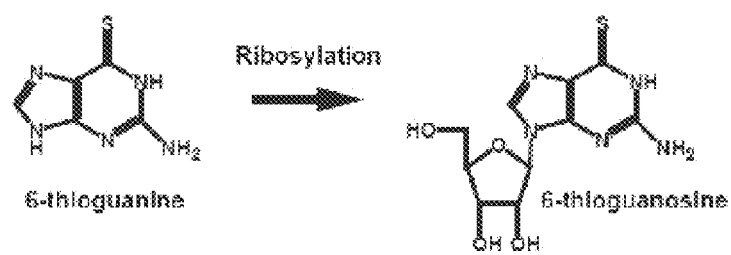
FIG. 6C shows that 6-thioguanine is able to be ribosylated and is incorporated into DNA and RNA (Swann et al., 1996), which likely causes its riboswitch-independent, non-specific antibiotic activity toward both *E. coli* and *S. aureus* (as shown in FIG. 6B).
Figure 7A:
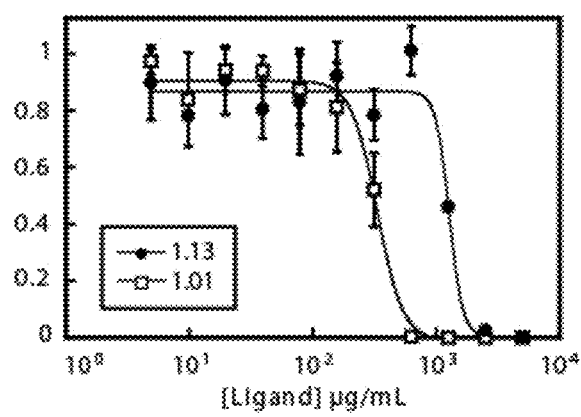
FIGS. 7A-D show the effect of various antibiotic compounds, including compounds 1.13 and 1.01, on the growth of *S. aureus* in vitro.
Figure 7B:
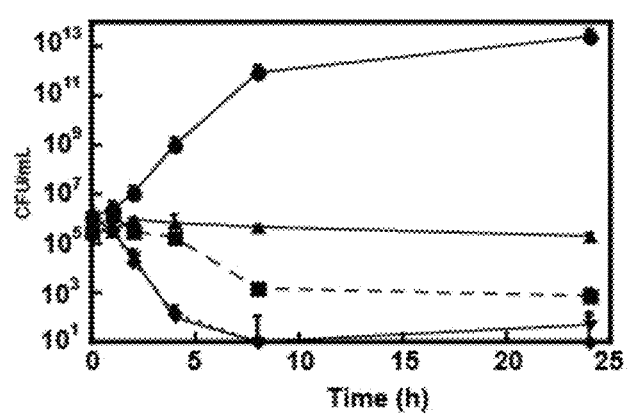
Figure 7C:
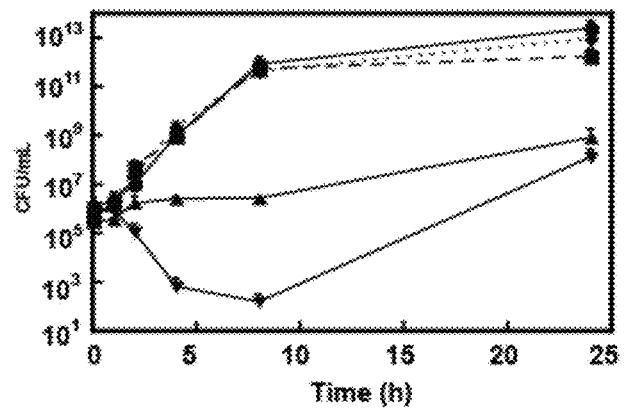
Figure 7D:
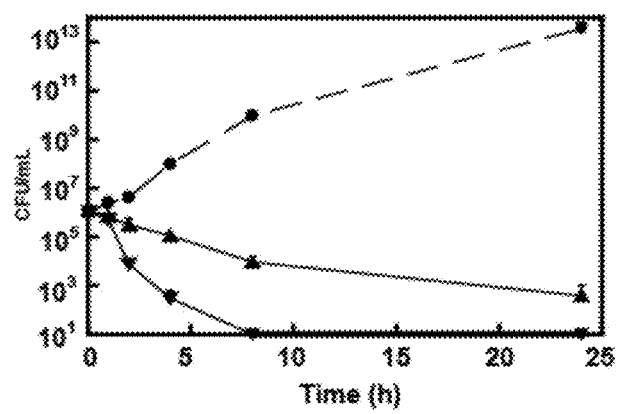

Shown schematically in FIG. 6A is the ribosylation reaction leading to the formation of nucleosides as well as examples of compounds of the invention that would prevent this ribosylation to occur. Asterisks (*) denote the position within the compound where chemical modification precludes ribosylation. FIG. 6B shows typical antibiograms performed as described in the previous example on strains of *E. coli* ATCC 35695 (which lacks a guaA riboswitch) and methicillin resistant *S. aureus* (which contains a guaA riboswitch) grown in the absence (1) or presence of 6-thio-guanine at a concentration of 0.5 mg/mL (2) or 1 mg/mL (3). FIG. 6C shows that 6-thioguanine is able to be ribosylated and is incorporated into DNA and RNA (Swann et al., 1996), which results in its riboswitch-independent, non-specific antibiotic activity toward both *E. coli* and *S. aureus* (as shown in FIG. 6B).

The effects of several antimicrobial compounds on the growth and survival of various strains of *E. coli* are summarized in Table 4 and presented in the form of minimum inhibitory concentrations (MIC, in µg/mL). Briefly, minimal inhibitory concentration of compounds 1.01 and 1.13 was determined using the microdilution method in 96-well microplates. Bacteria were inoculated at $10^5$ CFU/mL and incubated at 37° C. for 24 h in Muller-Hinton cation adjusted media. Then $OD_{595}$ nm was read on microplate reader.

TABLE 4

Minimum inhibitory concentrations (MIC) of various antibiotic compounds against *E. coli* strains

| Compounds | *E. coli* ATCC35695 | *E. coli* AcrAB—/— | *E. coli* Imp |
|---|---|---|---|
| Compound 1.01 | >5000 | >5000 | >5000 |
| Compound 1.13 | >5000 | >5000 | >5000 |
| Vancomycin | >128 | >128 | 0.25 |
| Erythromycin | 128 | 1.0-4.0 | 0.125-1.0 |

All concentrations are in µg/mL.

The results depicted in Table 4 above show that the guanine switch-less bacterium *Escherichia coli* is not inhibited by compounds 1.01 and 1.13 while the *E. coli* strain is highly permeable (strain *E. coli* Imp) to large antibiotic molecules like erythromycin and vancomycin or lacks the efflux pump AcrAB (strain *E. coli* AcrAB-/-) that is able to pump toxic molecules out of the cell. These results demonstrate the antimicrobial specificity of the compounds of the present invention (e.g., compounds 1.01 and 1.13) for bacteria that possess a guanine riboswitch controlling the expression of guaA. These results also demonstrate that the compounds of the present invention (e.g., compounds 1.01 and 1.13) are not broadly toxic to other bacteria lacking a guanine riboswitch controlling the expression of guaA. Thus, the compounds of the present invention allow for selective treatment of microbial pathogens affecting animals and humans. For example, compound 1.01 is sufficiently distinct from the natural guanine riboswitch ligand (guanine), to prevent incorporation of compounds into cellular nucleosides, nucleotides or nucleic acids, thus preventing toxicity for the mammalian or animal host in which such a compound is used for therapeutic intervention.

Example 6

Minimal Inhibitory Concentrations and Bactericidal Activities of Compounds of the Present Invention As disclosed herein, the compounds of the present invention (e.g., compounds 1.01 and 1.13) are able to specifically and selectively inhibit the growth and/or kill bacterial species that possess the guanine riboswitch controlling the expression of guaA such as *S. aureus* and *C. difficile*. The compounds of the present invention demonstrate an anti-bacterial effect on prototypical bacterial strains or bacterial stains causing persistent and chronic bovine mastitis in vitro (e.g., in culture media or milk) and in vivo (e.g., in mice mammary gland infections). Furthermore, the anti-bacterial effect of the compounds of the present invention (e.g., compound 1.01) is as rapid as that of the well-known antibiotic ciprofloxacin that is used in human and veterinary medicine.

The effect of various antibiotic compounds, including compounds 1.13 and 1.01, on the growth of *S. aureus* strain ATCC 29213 in vitro in Muller-Hinton cation adjusted media was tested and is shown in FIG. 7 and/or Table 5 below. For each experiment, bacteria were inoculated at a concentration of $10^5$ CFU/mL grown in Muller-Hinton cation adjusted media in the presence or absence of various antimicrobial compounds. After a specified time, bacteria were sampling and diluted in 96-well microplates before being inoculated on TSA plate. After 24 hours at 37° C., CFU were counted. FIG. 7A shows the growth of *S. aureus* strain ATCC 29213 as a function of ligand concentration for compounds 1.13 (●) and 1.01 (□). The MICs were determined using the microdilution method in 96-well microplates and the bacteria were incubated at 37° C. for 24 h following inoculation. The MIC for compound 1.13 was determined to be about 5000 µg/mL and that for compound 1.01 was determined to be about 600 µg/mL. FIGS. 7B and 7C show the growth of *S. aureus* strain ATCC 29213 as a function of time in the absence (●) or presence of various compounds. Specifically, FIG. 7B shows the anti-bacterial effect of the MIC corresponding to 0.5 µg/mL of erythromycin (▲), 1 µg/mL of vancomycin (●), 600 µg/mL of compound 1.01 (▼), and 0.5 µg/mL ciprofloxacin (♦). FIG. 7C shows the anti-bacterial effect in the absence (●) or presence of the same compounds at a dose of ¼ of their corresponding MICs (i.e., 0.125 µg/mL ciprofloxacin (♦), 0.125 µg/mL erythromycin (▲), 0.25 µg/mL vancomycin (■), 150 µg/mL compound 1.01 (▼)). FIG. 7D shows the growth of *S. aureus* strain ATCC 29213 as a function of time in media alone (●), in the presence of 600 µg/mL of compound 1.01 (▼), or in the presence of 600 µg/mL of compound 1.01 supplemented with 100 µM GMP (i.e. a molecule normally synthesized by the enzyme GMP synthetase encoded by guaA) (▲).

Example 7

Bactericidal Activity of Compound 1.01 on Various *S. Aureus* Strains

The bactericidal activity of compound 1.01 on various strains of *S. aureus* (including 3 chronic strains and 3 prototypical strains) was determined. These strains include prototypical *S. aureus* strains ATCC 29213, Newbould 305, SHY97-3906 as well as *S. aureus* strains isolated from persistent and chronic bovine mastitis cases (isolates #3, #557, #1290). *C. difficile* strain Cd6 was also examined. The bacteria were inoculated at $10^5$ CFU/mL in Muller-Hinton cation adjusted media in absence or presence of 600 µg/mL compound 1.01 and grown for 4 hours. The results are summarized in Table 5 below and are expressed as the mean fold reduction of CFU/mL (i.e., the number of CFU/mL of control bacteria divided by the number of CFU/mL of treated bacteria). These results indicate that compound 1.01 has a significant anti-bacterial effect against all the strains tested, with the highest effect being against *S. aureus* strain ATCC 29213.

TABLE 5

Bactericidal activity of compound 1.01 on
S. aureus and C. difficile strains

| Strains | Fold reduction of CFU/mL (control/treated) | |
|---|---|---|
| | Mean (log10) | SD |
| S. aureus ATCC 29213 | 6.67 | 0.58 |
| S. aureus Newbould 305 | 4.86 | 1.42 |
| S. aureus Chronic #3 | 5.11 | 1.25 |
| S. aureus Chronic #1290 | 5.42 | 1.56 |
| S. aureus Chronic #557 | 4.38 | 1.86 |
| S. aureus SHY97-3906 | 6.35 | 1.26 |
| C. difficile (Cd6) | 5.42 | 1.02 |

Example 8

Mode of Action of Compounds of the Present Invention

Figure 8A:
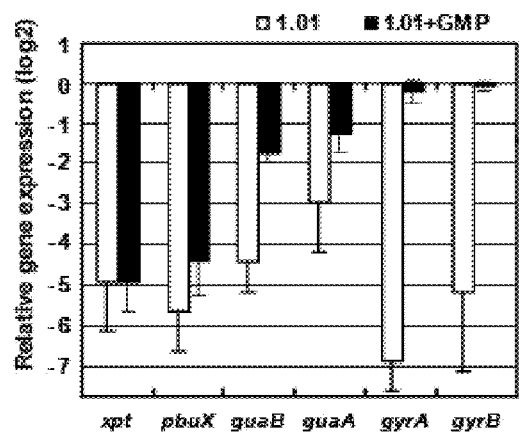
FIG. 8A shows the relative gene expression of several *S. aureus* genes under control of the guanine riboswitch (xpt, pbuX, guaA and guaB), when the bacteria are grown in vitro in the presence of compound 1.01 alone or in the presence of compound 1.01 supplemented with GMP. Gene expression was normalized to the expression level of xpt in the presence of compound 1.01. Genes gyrA and gyrB represent control genes encoding gyrase protein subunits whose expression is not down-regulated in the presence of GMP. Results represent the averages of three experiments and error bars represent standard deviations.
Figure 8B:
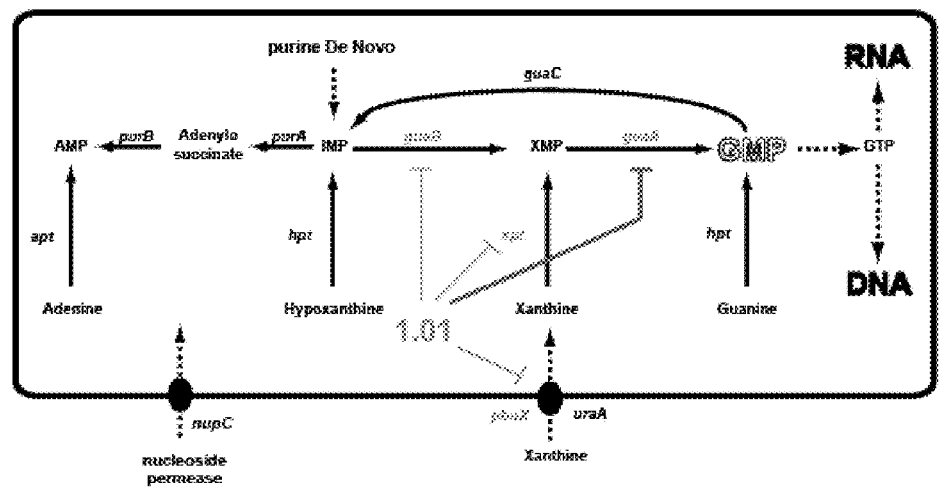
FIG. 8B shows a schematic representation of the inhibitory effect of compound 1.01 in *S. aureus*. A unique guanine riboswitch performs gene expression regulation of all four guanine-related genes (xpt, pbux, guaA and guaB). Riboswitch-regulated genes appear in grey and the compound 1.01 inhibitory effect is indicated by grey bars. A thick bar indicates the effect of compound 1.01 on expression of guaA. Broken arrows represent multiple synthesis steps that are not shown in the figure. Black ovals represent genes encoding various metabolite transporters.

To verify the specificity and explore the mechanism of action of compound 1.01, a transcriptomic microarray analysis was used to follow the expression of more then 500 S. aureus genes. Compound 1.01 was used alone or in combination with GMP and the results are shown in FIG. 8A. Briefly, the relative expression of S. aureus genes (xpt, pbuX, guaA and guaB) under the control of guanine riboswitch when grown in presence of compound 1.01 or compound 1.01 supplemented with GMP was examined. Bacteria were inoculated at $10^8$ CFU/mL in Muller-Hinton cation adjusted media in absence or presence of 600 µg/mL of compound 1.01 or 600 µg/mL compound 1.01 supplemented with 100 µM GMP. After 30 min of growth, RNA was extracted and 2.5 µg of RNA were submitted to reverse transcription to generate fluorescent probes through an aminoallyl cDNA labeling procedure before being hybridized on the microarray (Moisan et al., 2006). The experiments were repeated three times and the averages and standard deviations are shown. Gene expression was normalized to that of xpt in the presence of compound 1.01. The expression levels the genes gyrA and gyrB (encoding gyrase protein subunits) were also included as controls since their expression is not down-regulated in the presence of GMP. When compound 1.01 was used alone, more then 75% of genes were repressed including those controlled by the guanine riboswitch, xpt/pbuX/guaB/guaA (FIG. 8A). This could be explained by the inhibition of GMP production that is essential for the synthesis of messenger RNA (see FIG. 8B). When compound 1.01 and GMP were added in combination, the GMP allowed most of the studied genes to maintain their expression level and only 20% genes were repressed, among which were those controlled by the guanine riboswitch, xpt/pbuX/guaB/guaA (FIG. 8A). As depicted in FIG. 8B, the compounds of the present invention (e.g., compound 1.01) can interact with the guanine riboswitch and reduce expression of the genes xpt/pbuX/guaB/guaA. In particular, the inhibition of guaA causes a cellular depletion of the levels of GMP, which in turn inhibits general DNA and RNA synthesis. The supplementation of GMP counteracts the effects of the compounds of the present invention (e.g., compound 1.01) on DNA and RNA synthesis. These results demonstrate the specificity of compound 1.01 as shown on the schema of FIG. 8B.

FIG. 8B shows a schematic representation of the inhibitory effect of compound 1.01 in S. aureus. A unique guanine riboswitch performs gene expression regulation of all four guanine-related genes (xpt, pbux, guaA and guaB). Riboswitch-regulated genes appear in gray and the compound 1.01 inhibitory effect is indicated by grey bars. A thick bar indicates the effect of compound 1.01 on expression of guaA. Broken arrows represent multiple synthesis steps that are not shown in the figure. Ovals represent genes encoding various metabolite transporters.

Example 9

Inhibitory Effect of Compounds of the Present Invention During In Vivo Infection in Mice and Cows The compounds of the present invention (e.g., compound 1.01) are able to inhibit the growth and/or kill microbial pathogens possessing the guanine riboswitch controlling the expression of guaA during infection of the mammary glands in the mouse.

Figure 9:
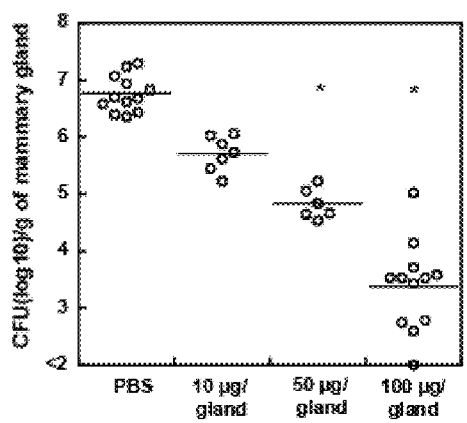
FIG. 9 presents the colony forming unit (CFU) count obtained from mice mammary gland homogenate previously infected with *S. aureus*. Mice mammary glands were treated 4 hours after infection with PBS with or without compound 1.01 at 10, 50 or 100 µg/gland. An asterisk indicates that the observed differences are statistically significant.

The efficacy of compound 1.01 in treating a S. aureus infection of the mouse mammary glands was examined. Briefly, mouse mammary glands were infected with 100 CFU of S. aureus. Four hours after the inoculation, the glands were treated with vehicle (PBS), 10, 50 or 100 µg/gland of compound 1.01. Six hours later, glands were excised, homogenized and plated on Mueller-Hinton agar. CFU were then counted after 18 hours at 35° C. The results of these studies are shown in FIG. 9. Each dot represents the CFU of each individual gland (n=6-12) and the median value for each group is indicated by the bar. Statistical differences (P<0.05) between CFU recovered from treated and untreated animals are shown by asterisks (non-parametric Kruskal-Wallis ANOVA with Dunn's post test). These results clearly demonstrate the anti-microbial effect in vivo of compound 1.01 against a S. aureus infection. This demonstrates that a compound such as compound 1.01 is sufficiently soluble, stable and bioavailable to display anti-microbial activity during an infection in an animal host. Intra-mammary injection of 10 times the effective dose of a compound such as compound 1.01 is able to reduce bacterial counts by >3 $\log_{10}$ without causing any significant signs of toxicity in mice, such as alterations in posture, breathing, piloerection or movement. There was also no apparent cytotoxicity upon histological observations of mammary tissues in 1.01-treated mice (100 µg/gland) compared to PBS-treated glands. Similarly, in tests performed in 4 Holstein cows over a period of 48 h, the intramammary injection of compound 1.01 at either 0 (saline control), 100 mg, 250 mg or 500 mg in the 4 individual quarters caused no change in body temperature, milk appearance, milk somatic cell counts or individual milk quarter production that could be correlated with any of the treatment.

Example 10

Figure 10:
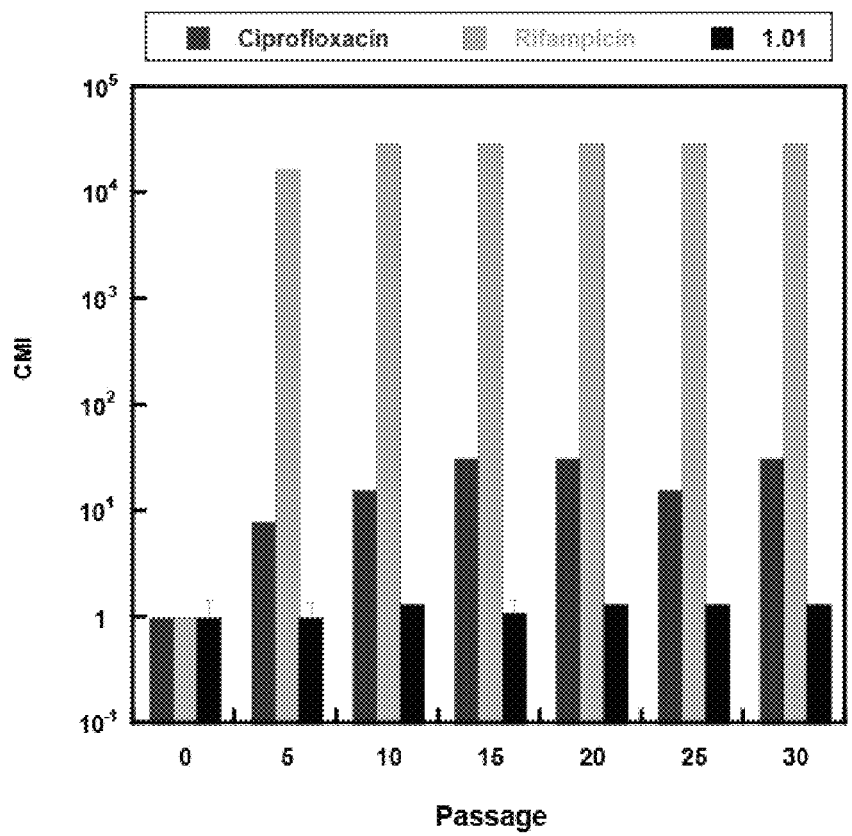
FIG. 10 shows the inability of *S. aureus* to develop resistance toward compound 1.01. The MIC of compound 1.01 on the growth of *S. aureus* strain ATCC 29213 was determined every 5 passages (up to 30 passages). For comparison, parallel results were obtained with two known antibiotics, ciprofloxacin and rifampicin.

Compounds of the Present Invention Prevent Rapid Development of Bacterial Resistance in S. Aureus The present invention relates to the discovery that the compounds of the present invention are not only able to inhibit the expression of the gene guaA when it is under riboswitch control, but can also prevent development of bacterial resistance. Specifically, FIG. 10 shows the inability of S. aureus to develop resistance toward compound 1.01. Briefly, serial passages in the presence of sub-inhibitory concentrations of test antibiotics demonstrating the inability of *S. aureus* to develop resistance toward 1.01 were conducted. The MIC of test compounds against *S. aureus* strain ATCC 29213 recovered from broth cultures containing sub-inhibitory concentrations of antibiotics was determined every 5 passages up to 30. As a comparison, results obtained with two known antibiotics, ciprofloxacin and rifampicin, were added to the histogram. High level resistance to ciprofloxacin and rifampicin was rapidly selected (within 5 daily passages) in *S. aureus*. Such rapid development of resistance for the traditional drugs is consistent with the selection of known single point mutations each able to provide a decrease in drug affinity for the bacterial cell target. There are at least 2 known point mutations in GyrA conferring resistance to ciprofloxacin in addition to possible over-expression of the NorA efflux pump system also occurring through mutations (at least 3 possible mutations) (Jones et al., 2000) and at least 17 possible different mutations in RpoB enabling resistance to rifampicin have been documented (Wilchelhaus et al., 2001). The *S. aureus* strain did not develop antibiotic resistance to compound 1.01 after at least 30 passages in culture. The absence of resistance observed in presence of 1.01 is probably because reestablishing guaA gene expression in the presence of 1.01 requires multiple mutational steps thus reducing the frequency of resistance development and/or that maintaining a functional riboswitch is a vital process that does not allow bacteria to bypass 1.01 antibiotic action. These results also strongly suggest that the compounds of the present invention not only possess an anti-microbial effect, but may also prevent the development of multi-drug resistant bacteria.

Example 11

Illustrative Compounds of the Present Invention

The present invention relates to a number of small molecule compounds having a selective antimicrobial activity on microbial pathogens containing guaA under control of the guanine riboswitch but having no substantial antimicrobial activity against microorganisms lacking a guaA-controlled by the guanine riboswitch. The compounds of the present invention fit the structural requirements for binding to the guanine riboswitch binding site and yet are chemically unable to be ribosylated by the targeted pathogens. The latter is meant at preventing incorporation of the compounds into cellular nucleosides, nucleotides or nucleic acids, and thus preventing broad, non-specific toxicity for the mammalian or animal host in which the present compounds are used for therapeutic intervention.

Figure 11:
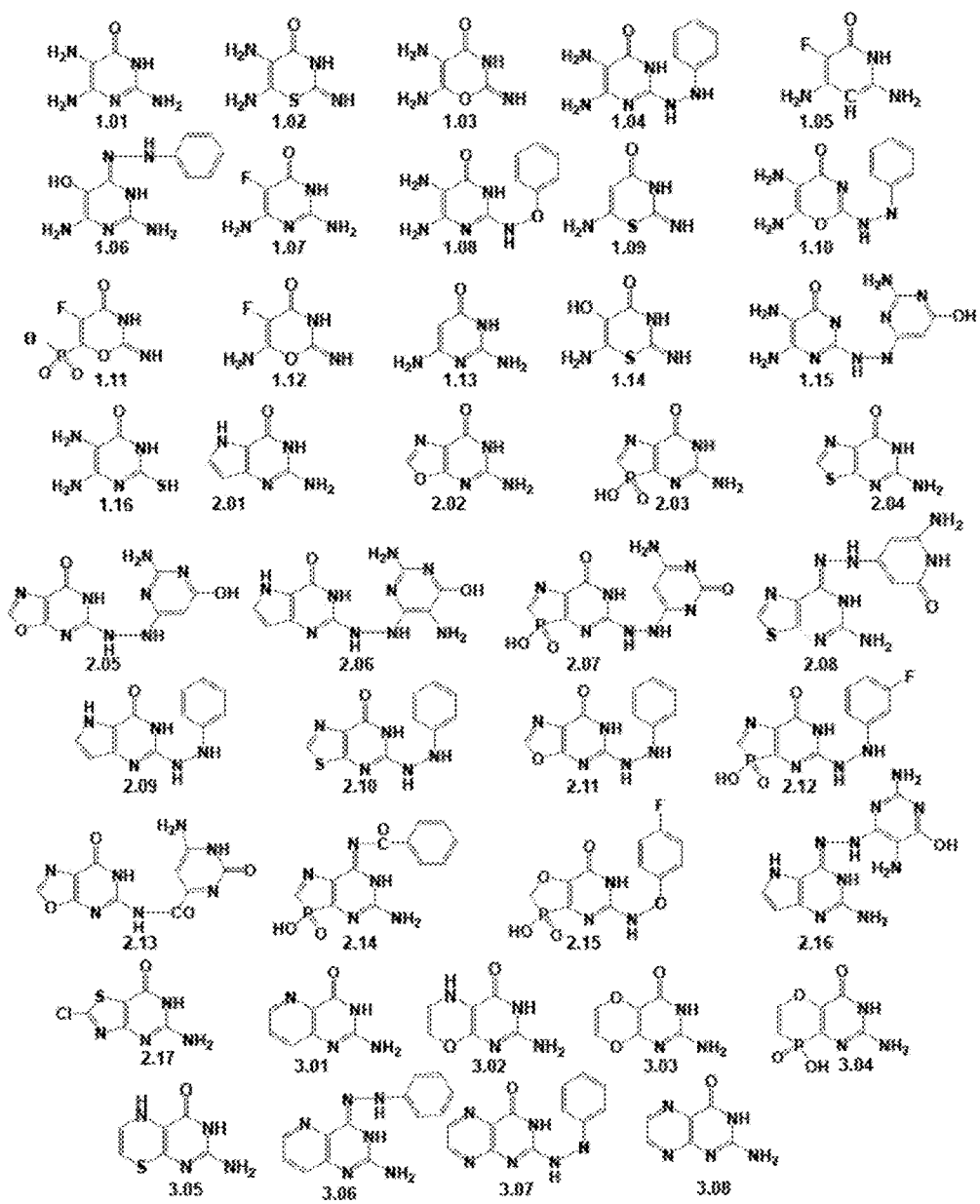
FIG. 11 shows examples of representative structures of compounds of the invention derived from formulas 1.0, 2.0 and 3.0. All examples are lacking the required chemistry to undergo ribosylation by bacterial or mammalian enzymes which could lead to broad and non-specific toxicity.

Representative structures of the compounds of the present invention derived from formulas 1.0, 2.0 and 3.0 are shown in FIG. 11. All these compounds are lacking the required chemistry to undergo ribosylation by bacterial or mammalian enzymes which could lead to broad and non-specific toxicity.

Example 12

Effect of Compounds of the Present Invention on the Treatment of Infections

In addition to intramammary infections, *S. aureus* is a pathogen also found in skin and skin structure infections, respiratory tract infections, blood and urine (Garau et al., 2009; Araki et al, 2002; Corey, 2009). *Clostridium* infections in humans such as those caused by *C. difficile, C. botulinum, C. tetani* and *C. perfringens* (Leffler and Lamont, 2009; Khanna, 2008), in poultry by *C. perfringens* (Van Immerseel et al., 2004) and in pigs are also of importance and the colonization of pigs by MRSA is also a problem linked to human health (Songer and Uzal, 2005; Khanna et al., 2008). The invention can therefore also be used for treatment of a variety of clostridial or staphylococcal infections occurring at body sites other than the mammary glands in animals and in humans.

Example 13

Aspects Relating to Synthesis of Compounds of the Present Invention

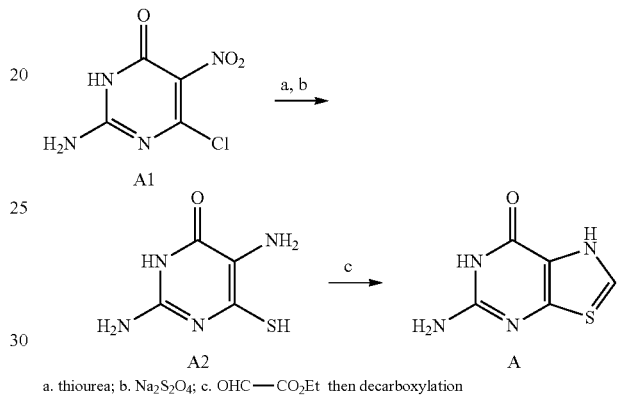

a. thiourea; b. Na₂S₂O₄; c. OHC—CO₂Et then decarboxylation

Analogue A can be synthesized from chloronitropyrimidine (A1) (Patel et al., 2007). Synthesis of A1 as described by Sircar et al., 1986 to give the precursor aminomercaptopyrimidine (A2). The latter can then be derivatized with ethyl oxoacetate to give the desired product A (R=H). This scheme will allow additional functionalization as well.

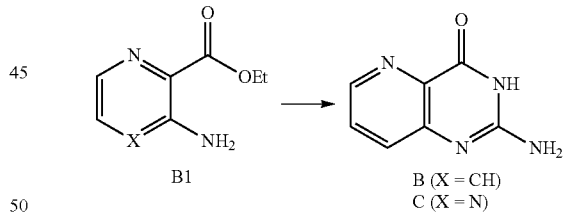

Pyridopyrimidine B can be synthesized following a procedure reported by Urleb et al., 1990 for a similar analogue. Pterin (X=N) is commercially available.

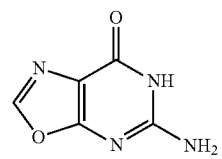

Oxazole derivative D was synthesized similarly to the synthesis of a methylated analogue (Miller et al, 2002).

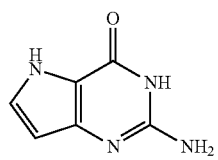

E

Pyrrole derivative E can be synthesized as described by Taylor and Young, 1995.

Example 14

Bio-Informatics Search of Guanine Riboswitches

Natural riboswitches contain aptamer domains which are typically very conserved in their sequence and structure given that they must bind cellular metabolites that are conserved through evolution. These aptamer domains exhibit a conserved scaffold of base-paired helices that organize the overall fold of each aptamer. The identities of each base in these helices most often reflect their need to be base-paired but in contrast, the identities of bases that are in direct contact with the bound metabolite are very highly conserved given precise role in the formation of the ligand binding site. Thus, it is possible to define a consensus sequence, representing all possible aptamer sequences, which can be used to perform computational searches in biological sequence databases. For instance, by translating the consensus sequence into an algorithm search, the software RNAmotif™ (Macke et al., 2001) can screen for all aptamer occurrences in the RefSeq™ microbial database (Pruitt et al., 2005). The output of the software gives genomic locations of all aptamer found. There is already a subgroup of aptamer sequences for various riboswitch families that have been retrieved by the scientific community that can be found at the Rfam™ database (Griffiths-Jones et al., 2005), but because it was observed that it is only partially complete, it was found preferable to build a database using RNAmotif™.

Below is an example of a consensus sequence used for the bioinformatic search. The meaningfulness of the characters and commands described in the consensus are very well described in the original RNAmotif™ article (Macke et al., 2001). This corresponds to possible guanine riboswitches that could adopt a similar structures than the known guanine riboswitch.

```
parms
wc += gu;
descr
h5( minlen=4, maxlen=10, mispair=0, ends='mm')
ss ( seq="^UA.\{0,1\}$")
h5( minlen=5, maxlen=8, mispair=3, ends='mm')
ss ( seq="^.\{0,1\}AU.\{0,3\}GG$" )
h3
ss ( seq="^GNNNCUAC$" )
h5( minlen=5, maxlen=8, mispair=2, ends='mm' )
ss ( seq="^CC.\{0,3\}A.\{0,1\}$")
h3
ss ( seq="^N\{0,1\}C.\{0,1\}$")
h3
H, Hoogsteen face; MI, mutual information; nt, nucleotides;
```

Example 15

Ability of Compounds of the Invention to Inhibit S. Aureus Growth

As disclosed herein, the compounds of the present invention (e.g., compounds 1.16, 2.02 and 2.17) (1.16 and 2.17 were purchased from Sigma-Aldrich and Toronto Research Chemical respectively) are able to specifically and selectively inhibit the growth and/or kill bacterial species that possess the guanine riboswitch controlling the expression of guaA such as S. aureus. As reported in Table 6 (below), compounds 1.16, 2.02 and 2.17 are able to bind guanine riboswitch and to inhibit S. aureus growth with a MIC of 0.128, 1.024 and 0.128 mg/mL, respectively.

The effect of the antibiotic compounds of formula 2.0, including compounds 2.02 and 2.17, on the growth of S. aureus strain ATCC 29213 in vitro in Muller-Hinton cation adjusted media allow to confirm the efficiency of compounds of general formula 2.0 to achieve antibiotic activity. For each compound, antibiotic activity was also tested on E. coli strain ATCC 35695 and no antimicrobial activity of the compounds (1.16, 2.02 and 2.17) was observed. The MICs were determined using the microdilution method in 96-well microplates and the bacteria were incubated at 37° C. for 24 h following inoculation.

As required, the compounds of Table 6 present no ribosylation site, so this will prevent their incorporation in DNA and their mutagenic potential.

TABLE 6

Description of the properties of various guanine riboswitch ligands

| Compound | Structure | Guanine riboswitch binding | S. aureus growth inhibition | Ribosylation | Appropriate properties |
|---|---|---|---|---|---|
| 1.16 | 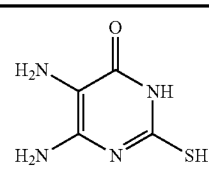 | Yes | Yes MIC 0.128 mg/mL | No | Yes |
| 2.02 | 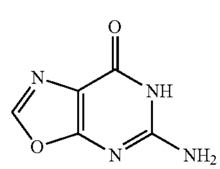 [SMILES: Nc1nc2ocnc2c(=O)[nH]1] | Yes | Yes MIC 1 mg/mL | No | Yes |

TABLE 6-continued

Description of the properties of various guanine riboswitch ligands

| Compound | Structure | Guanine riboswitch binding | S. aureus growth inhibition | Ribosylation | Appropriate properties |
|---|---|---|---|---|---|
| 2.17 | 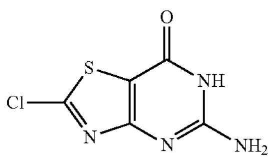 [SMILES: Nc1nc2nc(Cl)sc2c(=O)[nH]1] | Yes | Yes MIC 0.128 mg/mL | No | Yes |

Example 16

Route to Afford Compound 2.02: 5-Amino-6H-oxazolo[5,4-d]pyrimidin-7-one

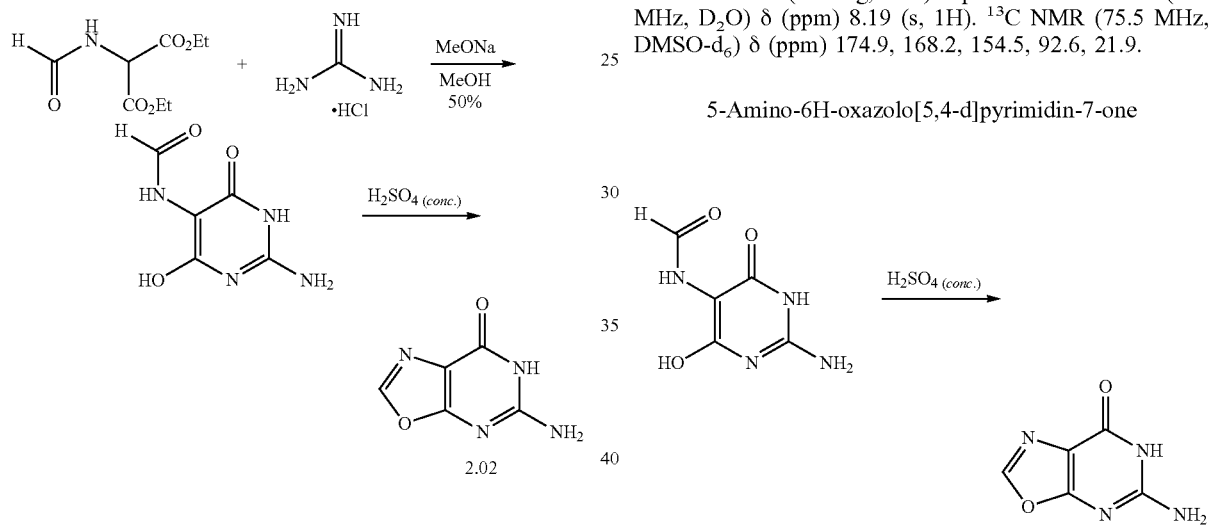

5-Formamino-2-amino-4,6-dihydroxypyrimidine

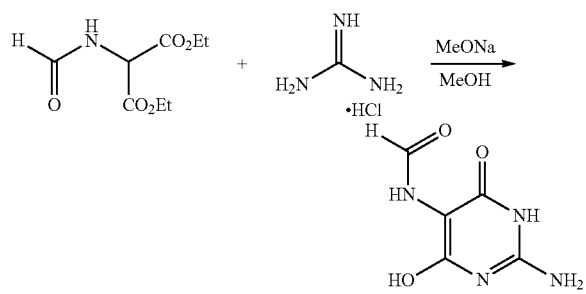

Sodium pieces (242 mg, 10.5 mmol) were added to MeOH (20 mL). After all the sodium had reacted, guanidine hydrochloride (1.00 g, 10.5 mmol) was added and the reaction mixture was stirred for 15 min. The reaction mixture was then heated to reflux and during this time, diethylacetamido malonate (2.13 g, 10.5 mmol) was added. After 2 h, more MeOH (20 mL) was added and the reaction mixture was refluxed overnight. The reaction mixture was then cooled to rt, filtered, washed with MeOH and chloroform and dried under vacuum at 50° C. The resulting solid was dissolved in water (25 mL) and was precipitated by the addition of 50% hydrochloric acid. The solution was filtered and the solid was washed with water and acetone and was finally dried under vacuum at 50° C. to afford compound 7 as a white solid (900 mg, 50%). mp >300° C. $^1$H NMR (300 MHz, D$_2$O) δ (ppm) 8.19 (s, 1H). $^{13}$C NMR (75.5 MHz, DMSO-d$_6$) δ (ppm) 174.9, 168.2, 154.5, 92.6, 21.9.

5-Amino-6H-oxazolo[5,4-d]pyrimidin-7-one

Compound 7 (125 mg, 0.73 mmol) was dissolved in 12 M H$_2$SO$_4$ (1.50 mL) using an ultrasonic bath. The dark yellow solution was stirred at rt overnight. THF (5 mL) was then added at 0° C. to form a yellow precipitate. The mixture was stored at 4° C. for 2 h and was centrifuged to obtain compound 8 as a yellow solid. $^1$H NMR (300 MHz, DMSO-d$_6$) δ (ppm) 8.71 (br s, 1H), 7.45 (br s, 1H). $^{13}$C NMR (75.5 MHz, DMSO-d$_6$) δ (ppm) 158.6, 152.3, 84.2. LRMS (m/z, relative intensity) 137 (MH$^+$—NH$_3$, 100), 153 (MH$^+$, 50), 159 (MNa$^+$—NH3, 90). HRMS calculated for C$_5$H$_6$N$_4$O$_3$: 153.0413, found: 152.9617.

Although the present invention has been described hereinabove by way of specific embodiments thereof, it can be modified, without departing from the spirit and nature of the subject invention as defined in the appended claims.

REFERENCES

Anderson, V. E., R. P. Zaniewski, F. S. Kaczmarek, T. D. Gootz, and N. Osheroff. 2000. Action of quinolones against Staphylococcus aureus topoisomerase IV: Basis for DNA cleavage enhancement. Biochem. 39:2726.

Anderson et al, The Practice of Medicinal Chemistry (1996), Academic Press, New York; and in The Orange Book (Food & Drug Administration, Washington, D.C. on their website).

Araki, M., R. Kariyama, K. Monden, M. Tsugawa, and H. Kumon. 2002. Molecular epidemiological studies of *Staphylococcus aureus* in urinary tract infection. J. Infect. Chemother. 8:168-174.

Barrick, J. E. and R. R. Breaker (2007) The distributions, mechanisms, and structures of metabolite-binding riboswitches, Genome Biol 8, R239.

Batey, R. T., S. D. Gilbert and R. K. Montange (2004) Structure of a natural guanine-responsive riboswitch complexed with the metabolite hypoxanthine, Nature 432, 411.

Berge, S. M., Bighley, L. D., Monkhouse, D. C. (1977) Pharmaceutical salts. J Pharm Sci. 66:1-19.

Blount K. F. and Breaker R. R. (2006) Riboswitches as antibacterial drug targets. Nature Biotechnology 24:1558-1564.

Coppins, R. L., Hall, K. B., Groisman, E. A. (2007) The intricate world of riboswitches. Curr Opin Microbiol. 10(2):176-181.

Corey, G. R. 2009. *Staphylococcus aureus* bloodstream infections: Definitions and treatment. Clin. Infect. Dis. 48 (suppl. 4):5254-5259.

Garau, J., E. Bouza, J. Chastre, F. Gudiol, and S. Harbarth. 2009. Management of methicillin-resistant *Staphylococcus aureus* infections. Clin. Microbiol. Infect. 15:125-136.

Griffiths-Jones, S., Moxon, S., Marshall, M., Khanna, A., Eddy, S. R., and Bateman, A. (2005) Rfam: annotating non-coding RNAs in complete genomes, Nucleic Acids Res. 33, D121-4.

Macke T J, Ecker D J, Gutell R R, Gautheret D, Case D A, Sampath R: RNAMotif, an RNA secondary structure definition and search algorithm. Nucleic Acids Res 2001, 29:4724-4735.

Jones, M. E., N. M. Boenink, J. Verhoef, K. Kohrer and F.-J. Schmitz. 2000. Multiple mutations conferring ciprofloxacin resistance in *Staphylococcus aureus* demonstrate long-term stability in an antibiotic-free environment. J. Antimicrob. Chemother. 45:353-356.

Khanna, N. 2008. Clindamycin-resistant *Clostridium perfringens* cellulitis. J. Tissue Viability 17:95-97.

Khanna, T., R. Friendship, C. Dewey, J. S. Weese. 2008. Methicillin resistant *Staphylococcus aureus* colonization in pigs and pig farmers. Vet. Microbiol. 128:298-203.

Knowles D. J., Foloppe N., Matassova N. B., Murchie A. I. The bacterial ribosome, a promising focus for structure-based drug design. Current opinion in pharmacology 2002. 2:501-502.

Leffler, D. A., and J. T. Lamont. 2009. Treatment of *Clostridium difficile*-associated disease. Gastroenterology 136:1899-1912.

Mayer, S. J., A. E. Watennan, P. M. Keen, N. Craven, and F. J. Bourne (1988) Oxygen concentration in milk of healthy and mastitic cows and implications of low oxygen tension for the killing of *Staphylococcus aureus* by bovine neutrophils. J. Dairy Res. 55:513.

Miller, D. J., Ravikumar, K., Shen, H., Suh, J.-K., Kerwin, S. M., and Robertus, J. D. (2002) J. Med. Chem. 45:90-98.

Moisan, H., E. Brouillette, C. L. Jacob, P. L. Begin, S. Michaud, and F. Malouin. 2006. The Transcription of Virulence Factors in *Staphylococcus aureus* Small Colony Variants Isolated from Cystic Fibrosis Patients is Influenced by SigB. J. Bacteriol. 188:64-76.

Mulhbacher, J. and D. A. Lafontaine (2007) Ligand recognition determinants of guanine riboswitches. Nucleic Acids Res 35:5568.

Patel, P. R., Ramalingan, C., Park, Y. T. (2007) Synthesis and antimicrobial evaluation of guanylsulfonamides. Bioorg Med Chem Lett. (2007) 17:6610-4.

Pruitt, K., Tatusova, T., and Maglott, D. 2005. NCBI Reference Sequence (RefSeq): A curated nonredundant sequence database of genomes, transcripts, and proteins. Nucleic Acids Res. 33: D501-D504. doi: 10.1093/nar/gki011.

Russo, T. A., S. T. Jodush, J. J. Brown, and J. R. Johnson. (1996) Identification of two previously unrecognized genes (guaA and argC) important for uropathogenesis. Mol. Microbiol. 22:217-229.

Samant, S., H. Lee, M. Ghassemi, J. Chen, J. L. Cook, A. S. Mankin, and A. A. Neyfakh. (2008) Nucleotic biosynthesis is crucial for growth of bacteria in human blood. PloS Pathogens 4(2):e37 (0001-0010).

Sears, P. M. and K. K. McCarthy (2003) Management and treatment of staphylococcal mastitis. Vet. Clin. Food Anim. Pract. 19:171-185.

Sircar, J. C., Suto, M. J., Scott, M. E., Dong, M. K., Gilbertsen, R. B. (1986) Inhibitors of human purine nucleoside phosphorylase. Synthesis, purine nucleoside phosphorylase inhibition, and T-cell cytotoxicity of 2,5-diaminothiazolo[5,4-d]pyrimidin-7(6H)-one and 2,5-diaminothiazolo[4,5-d]pyrimidin-7(6H)-one. Two thio isosteres of 8-aminoguanine. J Med Chem. 1986 September; 29(9):1804-6.

Songer, J. G., and F. A. Uzal. 2005. Clostridial enteric infections in pigs. J. Vet. Diagn. Invest. 17:528-536.

Swann, P. F., Waters, T. R., Moulton, D. C., Xu, Y. Z., Zheng, Q., Edwards, M., Mace, R. Role of postreplicative DNA mismatch repair in the cytotoxic action of thioguanine. (1996) Science. 273(5278):1109-11.

Talbot G H, Bradley J, Edwards J E Jr, Gilbert D, Scheid M, Bartlett J G; Antimicrobial Availability Task Force of the Infectious Diseases Society of America. Clin Infect Dis. 2006 42:657-658

Taylor, E. C., Young, W. B. (1995) Pyrrolo[3,2-d]pyrimidine folate analogues: "inverted" analogues of the cytotoxic agent LY231514. J Org Chem. 60:7947-52.

Tiedeman, A., J M Smith and H Zalkin. 1985. Nucleotide Sequence of the guaA gene encoding GMP synthetase of *Escherichia coli* K12. J. Biol. Chem. 260:8676-79.

Urleb, U., Stanovnik, B., Tisler, M. (1990) The Synthesis and Transformations of 2-Ethoxycarbonyl-3-Isothiocyanatopyridine. Pyrido[3,2-d]pyrimidines and some Azolo-pyrido[3,2-d]pyrimidines. J. Het. Chem. 27:407-12.

Van Immerseel, F., J. De Buck, F. Pasmans, G. Huyghebaert, F. Haesebrouck, and R. Ducatelle. 2004. *Clostridium perfringens* in poultry: an emerging threat for animal and public health. Avian Pathol. 33:537-549.

Wilchelhaus, T. A., V. Schafer, V. Brade and B. Boddinhaus. 2001. Differential effect of rpoB mutations on antibacterial activities of rifampicin and KRM-1648 against *Staphylococcus aureus*. J. Antimicrob. Chemother. 47:153-156.

WO 2006/055351, Breaker R. et al., 2006.

The invention claimed is:

1. A method of treating a bacterial infection in a subject, said method comprising administering to said subject a therapeutically effective amount of a non ribosylable ligand of a guanine riboswitch, wherein said subject is infected by the bacterial infection prior to said administration, wherein said bacterial infection is caused by a pathogen bearing the guanine riboswitch, and wherein the guanine riboswitch controls the expression of guaA, wherein said pathogen:
  a) belongs to the genus *Staphylococcus* or *Clostridium*; or
  b) is *Alkaliphilus metalliredigens; Alkaliphilus oremlandii; Bacillus anthracis; Bacillus cereus; Bacillus halodurans; Bacillus thuringiensis; Bacillus weihenstephanensis; Exiguobacterium sibiricum; Geobacillus kaustophilus; Geobacillus thermodenitrificans; Lysinibacillus sphaericus; Oceanobacillus iheyensis; Thermoanaerobacter pseudethanolicus*; or *Thermoanaerobacter* X514, and
  wherein said non ribosylable ligand of guanine riboswitch is the compound 4-hydroxy-2,5,6-triaminopyrimidine (1.01) or a pharmaceutically acceptable salt, solvate or stereoisomer thereof.

2. The method of claim 1, wherein said subject is a cow or a human.

3. The method of claim 1, wherein said pathogen is *Staphylococcus aureus,* methicillin-resistant *Staphylococcus aureus, Staphylococcus epidermidis, Staphylococcus haemolyticus, Clostridium botulinum* or *Clostridium difficile.*

4. The method of claim 1, wherein said infection is a mammary gland infection.

5. The method of claim 1, wherein said pathogen is a pathogen belonging to the genus *Staphylococcus* or *Clostridium* and wherein said pathogen is *Staphylococcus aureus; Staphylococcus carnosus; Staphylococcus epidermidis; Staphylococcus haemolyticus, Staphylococcus saprophyticus, Clostridium acetobutylicum; Clostridium beijerinckii; Clostridium botulinum; Clostridium difficile; Clostridium novyi; Clostridium perfringens* or *Clostridium tetani.*

* * * * *